United States Patent [19]

Szmuszkovicz

[11] 4,145,435
[45] Mar. 20, 1979

[54] 2-AMINOCYCLOALIPHATIC AMIDE COMPOUNDS

[75] Inventor: Jacob Szmuszkovicz, Kalamazoo, Mich.

[73] Assignee: The Upjohn Company, Kalamazoo, Mich.

[21] Appl. No.: 741,354

[22] Filed: Nov. 12, 1976

[51] Int. Cl.$^2$ .................... C07D 207/06; A61K 31/40
[52] U.S. Cl. ................. 424/274; 260/239 A;
546/205; 546/216; 546/222; 546/229; 546/233;
546/234; 546/240; 546/238; 546/239;
260/376.33; 260/376.4; 260/558 A; 424/244;
424/250; 424/267; 424/32; 544/400; 544/402;
544/401; 544/399; 548/335; 548/336
[58] Field of Search .......... 260/326.4, 326.33, 293.76,
260/268 R, 293.56, 558 A, 268 BC, 239 A;
424/274, 267, 320, 244, 250; 544/400

[56] References Cited

U.S. PATENT DOCUMENTS

| | | | |
|---|---|---|---|
| 3,510,492 | 5/1970 | Szmuszkovicz | 260/293.76 |
| 3,647,804 | 3/1972 | Rynbrandt et al. | 260/293.63 |
| 3,772,308 | 11/1973 | Krapcho | 260/293.76 |
| 3,852,347 | 12/1974 | Krapcho | 260/293.76 |

OTHER PUBLICATIONS

Winternitz et al; Societe Chemique de France Bulletin, Series 5, 23, pp. 382-391 (1956).
Harper et al; J. Chem. Soc. (London) pp. 4280-4284 (1964).
Brittain et al, But. J. of Pharm. vol. 49, pp. 158-159 (1973).

Primary Examiner—Nicholas S. Rizzo
Assistant Examiner—Mary Lee
Attorney, Agent, or Firm—John T. Reynolds

[57] ABSTRACT

Cis- and trans-N-(2-aminocycloaliphatic)-2-arylacetamide derivative compounds of the formula

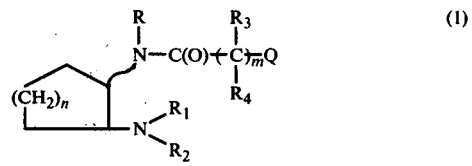

e.g., N-[2-(N', N'-dimethylamino)cyclohexyl]-N-methyl-2-(4-bromophenyl)acetamide and trans-N-methyl-N-[2-(1-pyrrolidinyl)cyclohexyl]acetamide, 2-(3,4-dichlorophenyl) and their pharmaceutically acceptable salts, have been found to have potent analgesic activity, and the preferred compounds have in addition only low to moderate apparent physical dependence liability, compared to morphine and methadone. As analgesics they would be useful also as antitussives. Processes for preparation of these compounds are also disclosed. This invention also includes compositions containing these compounds useful in pharmaceutical dosage unit form for alleviating pain in humans and animals, as well as methods for alleviating pain in animals and humans with these compositions.

28 Claims, No Drawings

2-AMINOCYCLOALIPHATIC AMIDE COMPOUNDS

INTRODUCTION

This invention relates to N-(2-amino-cycloaliphatic) aryl acylamide compounds. More particularly, this invention provides some new N-(2-amino-cycloaliphatic) phenylacetamide compounds which have useful analgesic activity and narcotic antagonist activity. Processes for their preparation are also disclosed.

BACKGROUND OF THE INVENTION

Szmuszkovicz U.S. Pat. No. 3,510,492 discloses and claims some 2-anilino- and 2-anilinomethylcycloalkylamines which are useful as antidiabetic drugs in that they can be administered in low dosages for reducing blood sugar. However, that patent does not teach or suggest the compounds of this invention or the uses which have been found for these compounds. This '492 patent also discloses but does not claim compounds of the formula

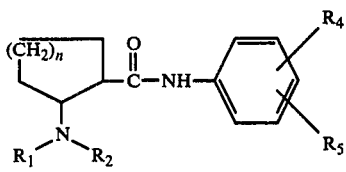

as compounds of structure XV in column 4 thereof, where n is 1 to 4, $R_1$ and $R_2$ are hydrogen, $C_1$ to $C_4$-alkyl, benzyl or $R_1$ and $R_2$ together with the nitrogen to which they are bonded denote a cyclic amino group of the formula

containing 5 to 9 nuclear atoms, and $R_4$ and $R_5$ are hydrogen, $C_1$ to $C_4$-alkyl, $C_1$ to $C_4$-alkoxy, hydroxy, halogen or trifluoromethyl. Intermediate compounds of formula XVII in column 4 of that '492 patent have the formula

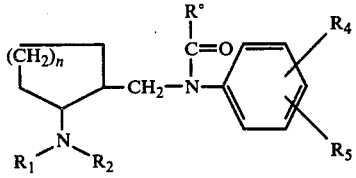

wherein R° is hydrogen or $C_1$ to $C_3$-alkyl, and $R_4$ and $R_5$ are described above, but the structures and uses are different from the compounds disclosed and claimed herein.

Rynbrandt et al. U.S. Pat. No. 3,647,804 discloses some 2-amino-cycloalkane-1-carboxamides and diamines which are said to be useful pharmaceutical drugs because of their hypoglycemic, sedative and anti-inflammatory activities, but that patent does not suggest the amide types of this invention or the pharmacological activities claimed for the compounds of this invention. F. Winternitz, et al., in Bull. Soc. Chim., (France), 382 (1956) disclose the compound N-(2-dimethylaminocyclohexy)benzamide for the purpose of obtaining a solid derivative of the liquid diamino compound but that article contains no reference to biological data.

N. J. Harper et al. in J. Chem. Soc. 4280 (1964) disclose the compounds of the formula

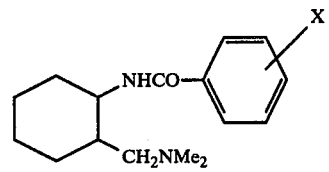

where X is hydrogen, m-fluoro or p-chloro. The stereochemistry of those compounds was not indicated with certainty. In a hot plate test, using pethidine (meperidine) as standard (activity = 1) the analgesic activity of these amide compounds where X was p-chloro was 0.22. In the electroshock test it was 35% as active as diphenylhydantoin, but all of these compounds lacked activity in the antiamphetamine and antireserpine tests.

R. T. Brittain et al. in Brit. J. Pharm., 49, 158P (1973) and N. J. Harper, et al. in Journal of Medicinal Chemistry, (1974), Vol. 17, pp 1188–1193 disclose some 1-amino-1-benzamidomethylcyclohexane analgesic compounds of the formulae:

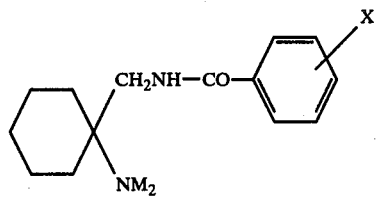

wherein X is hydrogen, 4-F, 3,4-di-Cl, 2-Cl, 3-Cl or 4-Cl;

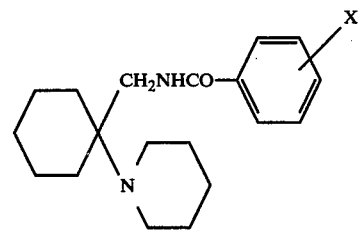

where X is 4-fluoro, 3,4-dichloro or 2-chloro or 2-chloro; and

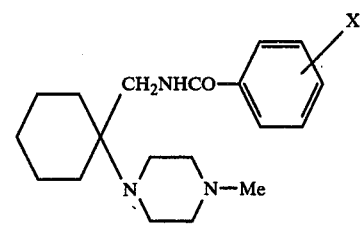

where X is hydrogen or 3,4-dichloro, but these compounds are not 1,2-cyclohexyldiamine derivatives, as are the compounds of this invention.

Those skilled in the analgesic art continue to search for new and useful compounds.

OBJECTS OF THE INVENTION

It is an object of the invention to provide some new acylamido derivatives of 1,2-diaminocycloaliphatic compounds which are useful as analgesic compounds.

It is a more specific object of this invention to provide some new 2-aminocycloaliphatic arylamide compounds which have useful analgesic properties and the preferred compounds also having only low to moderate apparent physical dependence liability compared to the high apparent physical dependence liability to some known useful drugs such as morphine and methadone, and the moderate apparent dependence liability of some known useful drugs such as dextropropoxyphene, and codeine.

Other objects, aspects and advantages of this invention will become apparent from reading the remaining specification and claims which follow.

SUMMARY OF THE INVENTION

Briefly, this invention provides some new N-(2-amino cycloaliphatic)-1-phenylacetamide derivative compounds which have been found to possess useful ranges of analgesic and narcotic antagonist properties while also having low apparent physical dependence liability. This invention also includes pharmaceutical compositions containing these compounds as an active analgesic component and the method of inducing analgesic activities in an animal patient, including humans, by administering one of these new compounds in an amount sufficient to induce analgesic activity. This invention also relates to new compounds in pharmaceutical dosage unit forms useful for the relief of pain regardless of origin, for example, traumatic pain, bone pain, cancer pain, post surgical pain, homotopic pin, menstrual pain, headache and the like. The list is not intended to be exhaustive of the types of pains for which the inventive compounds and the formulations thereof can be used.

DETAILED DESCRIPTION OF THE INVENTION

More particularly, this invention provides some new compounds of the formula (1)

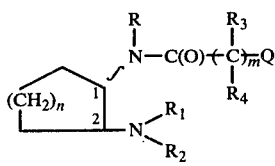

wherein the ~ symbol at the 1-position of the cycloaliphatic ring denotes cis- or trans-stereo configuration of the 1-position substituent with respect to the substituent in position 2 of the same cycloaliphatic ring;

R is hydrogen or $C_1$ to $C_3$-alkyl;

$R_1$ and $R_2$, taken separately are hydrogen, $C_1$ to $C_3$-alkyl, or when $R_1$ is hydrogen or $C_1$ to $C_3$-alkyl, $R_2$ is $C_1$ to $C_6$-alkyl, $-CH_2CF_3$, $C_3$ to $C_6$-(allylic)alkenyl, $C_2$ to $C_5$-hydroxalkyl, $C_3$ to $C_6$-cycloalkyl, $C_3$ to $C_4$-cycloalkylmethyl, phenyl-$C_1$ to $C_3$-alkyl,- or $R_1$ and $R_2$, taken together with the nitrogen to which they are bonded complete a saturated, monocyclic nitrogen heterocyclic ring containing only carbon and nitrogen ring atoms and containing from 3 to 5 carbon atoms and not more than two nitrogen ring forming atoms; said saturated, monocyclic nitrogen heterocyclic rings having 3 to 4 ring carbon atoms permissively being substituted in the 3-position of the ring with hydroxy, $C_1$ to $C_3$-alkyloxy or $C_1$ to $C_3$-alkanoyloxy, and said saturated heterocyclic rings having five ring carbon atoms permissively being substituted in the 3- or 4-positions with hydroxy, $C_1$ to $C_3$-alkanoyloxy, or $C_1$ to $C_3$-alkyloxy; said saturated monocyclic nitrogen heterocyclic ring including an N-piperazinyl ring, permissively substituted on the N'-nitrogen with $C_1$ to $C_3$-alkyl;

$R_3$ is hydrogen or methyl;

$R_4$ is hydrogen or methyl, or $R_3$ and $R_4$ can be taken together with the carbon to which they are bonded to complete a cyclopropylene ring;

m is 1 to 4, and is 2 to 4 only when $R_3$ and $R_4$ are both hydrogen;

n is 1 to 8;

Q is 1-naphthyl, 2-naphthyl or

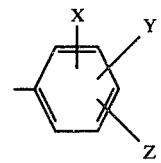

wherein each of X, Y and Z is hydrogen, a halogen having an atomic number of from 9 to 35, trifluoromethyl, $C_1$ to $C_3$-alkyl, $C_1$ to $C_3$-alkyloxy, azido($-N_3$) or phenyl, and at least one of X, Y and Z is a substituent other than hydrogen, and when one of X, Y and Z is azido, phenyl, $C_1$ to $C_3$-alkyloxy or trifluoromethyl, the remaining X, Y and Z moieties are hydrogen and when R is hydrogen at least two of X, Y and Z are substituents other than hydrogen; and the pharmaceutically acceptable salts thereof.

The compounds of formula I or their acid addition salts in their crystalline state may be isolated as solvates, i.e., with a discrete quantity of solvent, e.g., water, ethyl acetate, methanol, and the like, associated physically, and thus removable without effective alteration of the chemical entity per se.

In the above illustrated structure (I) the wavy line (bond) at the 1-position of the cycloaliphatic ring will be recognized by those skilled in the chemical art as a symbol to denote the likelihood for cis- or trans-stereochemistry of the 1-position substituent with respect to the substituent in position 2 of the same cycloaliphatic ring. It will also be recognized by those skilled in the chemical art that each of the points of attachment (at positions 1- and 2) in the cycloaliphatic ring is chiral and can thus independently possess a R- and S- configuration. Therefore, there can exist trans-d-, trans-l-, cis-d- and cis-l-optical stereoisomers in addition to cis and trans -dl of these compounds. Methods of preparing the various forms are described below.

Preferred subgroups of formula I compounds are those in which the amino substituents are trans to each other.

In the above formula I compounds the term "$C_1$ to $C_3$-alkyl" means methyl ethyl, n-propyl and isopropyl groups. The term "$C_1$ to $C_6$-alkyl" includes the above $C_1$ to $C_3$-alkyl groups as well as the butyl, pentyl and hexyl groups in their various isomeric forms. The term "$C_3$ to $C_6$-(allylic) alkenyl" is intended to include the non-adjacent double bond groups, e.g., allyl, 2- butenyl, 2-pentenyl and 2, -hexenyl groups. In the compounds containing a $C_2$ to $C_5$-hydroxyalkyl group, the hydroxy moiety cannot be on the carbon adjacent to the nitrogen. The cycloalkyl groups include the cyclopropyl, cyclobutyl, cyclopentyl and cyclohexyl radicals. The $C_1$ to $C_3$-alkyloxy substituents include the methoxy, ethoxy, propyloxy and isopropyloxy groups. The $C_1$ to $C_3$-alkanoyloxy include the formyloxy, acetyloxy and propionoxy groups. Examples of saturated, monocyclic nitrogen heterocyclic ring groups include azetidinyl, pyrrolidinyl, piperidinyl groups.

A preferred subgroup of these formula I compounds are those wherein R is $C_1$ to $C_3$-alkyl; $R_1$ and $R_2$ are each $C_1$ to $C_3$-alkyl; $R_3$ and $R_4$ are each hydrogen; n is 2, m is 1; Q is

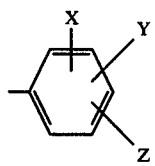

wherein at least one of X, Y and Z is a halogen having an atomic number of from 9 to 35 or azido, and when X is azido, Y and Z are hydrogen; and the pharmacologically acceptable salts thereof. Examples of compounds of this preferred group include N-[2-(N,N-dimethylamino)-cyclohexyl]-N-methyl-2-(4-bromophenyl)acetamide, N-[2-(N,N-dimethylamino)cyclohexyl]-N-methyl-2-(3,4-dichlorophenyl)acetamide, and N-[2-(N,N-dimethylamino)cyclohexyl]-N-methyl-2-(4-azidophenyl)acetamide, and pharmaceutically acceptable salts thereof.

Another preferred group of these compounds are those compounds of formula I above wherein R is $C_1$ to $C_3$-alkyl, $R_1$ and $R_2$ are taken together with the nitrogen to which they are bonded to complete a saturated, monocyclic nitrogen heterocyclic ring containing 3 to 5 ring carbon atoms; $R_3$ and $R_4$ are each hydrogen; n is 2; m is 1; and Q is

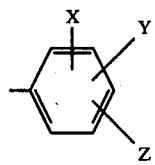

wherein at least one of X, Y and Z is a halogen having an atomic number of 9 to 35 or azido, and when X is azido Y and Z are hydrogen and pharmacologically acceptable salts thereof. Examples of compounds of this preferred subgroup include N-[2-(1-pyrrolidinyl)cyclohexyl]-N-methyl-2-(4-bromophenyl)acetamide; N-[2-(1-pyrrolidinyl)-cyclohexyl]-N-methyl-2-(3,4-dichlorophenyl)acetamide; and N-[2-(1-piperidinyl)cyclohexyl]-N-methyl-2-(4-azidophenyl)acetamide, and pharmacologically acceptable salts thereof.

Other closely related preferred compunds of this invention are those of formula I above wherein R is $C_1$ to $C_3$-alkyl, $R_1$ and $R_2$ are taken together with the nitrogen to which they are bonded to complete a saturated monocyclic nitrogen heterocyclic ring containing 3 to 5 carbon atoms; $R_3$ is hydrogen and $R_4$ is methyl; n is 2; m is 1 and Q is

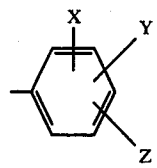

wherein at least one of X, Y and Z is a halogen having an atomic number of from 9 to 35, or azido, and if X is azido Y and Z are hydrogen and the pharmacologically acceptable salts thereof. Examples of compounds in this preferred group include N-methyl-N-[2-(N-pyrrolidinyl)cyclohexyl]-2-(3,4-dichlorophenyl)propionamide; N-[2-(N-pyrrolidinyl)cyclohexyl]-2-(4-bromophenyl)propionamide; and N-ethyl-N-[2-(N-azetidinyl)cyclohexyl]-2-(4-azidophenyl)propionamide; and the pharmacologically acceptable salts thereof.

Also, compounds of formula I above wherein R is $C_1$ to $C_3$-alkyl, $R_1$ and $R_2$ are each $C_1$ to $C_3$-alkyl; $R_3$ and $R_4$ are each hydrogen, n is 2; m is 1; and Q is

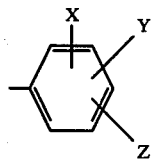

wherein at least one of X, Y and Z is a $C_1$ to $C_3$-alkyl are a preferred subgroup.

Preferred compounds of formula I which have larger ring systems include:

(A) Those having larger aryl groups in the Q position, e.g., those wherein R is $C_1$ to $C_3$-alkyl; $R_1$ and $R_2$ are each $C_1$ to $C_3$-alkyl; $R_3$ and $R_4$ are each hydrogen; n is 2; m is 1; and Q is 1-naphthyl or 2-naphthyl. Examples of compounds of this preferred group are:
N-[2-(N',N'-dimethylamino)cyclohexyl]-N-methyl-2-(1-naphthyl)acetamide;
N-[2-(N',N'-dimethylamino)cyclohexyl]-N-methyl-2-(2-naphthyl)acetamide; and (B) those having larger cycloaliphatic ring moieties wherein R is $C_1$ to $C_3$-alkyl, $R_1$ and $R_2$ are each $C_1$ to $C_3$-alkyl; $R_3$ and $R_4$ are each hydrogen; n is 3 to 8; and m is 1; and Q is

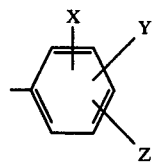

wherein at least one of X, Y and Z is a halogen having an atomic number of from 9 to 35, $C_1$ to $C_3$-alkyl, or azido, and when X is azido, Y and Z are hydrogen and the pharmacologically acceptable salts thereof. Examples of these preferred compounds include N-[2-(N',N'-dimethylamino)cycloheptyl]-N-methyl-2-(4-bromophenyl)acetamide; N-[2-(N',N'-dimethylamino)cyclooctyl]-N-methyl-2-(4-bromophenyl)acetamide; N-[2-(N',N'-diethylamino) cyclooctyl]-N-methyl-2-(4-azidophenyl)acetamide; N-[2-(N',N'-dipropylamino)cyclododecyl]-N-methyl-2-(3,4-dichlorophenyl)-acetamide; and the pharmacologically acceptable salts thereof.

In general and with the exception described hereinbelow, these new amide compounds of this invention can be prepared by reacting the appropriate 1,2-cycloaliphatic diamine of the formula

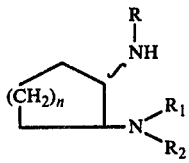  (II)

with an aracyl imidazole of the formula

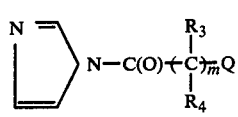  (III)

wherein R, $R_1$, $R_2$, $R_3$, $R_4$, n, m, and Q are defined above, or with an acyl halide of the formula

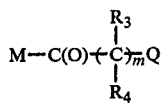  IV wherein M is chloride or bromide and $R_3$, $R_4$, m and Q are as defined above, in an organic solvent for the reactants, preferably in a cyclic ether solvent such as tetrahydrofuran (THF) or dioxane, or the like, until the compound of this invention is produced. The reactants, (II) and (III) or (II) and (IV) can be mixed in substantially equimolar proportions to effect formation of the desired product (I), but if one of the reactants (II), (III) and (IV) is more expensive than the other, it is sometimes preferred to use a stoichiometric excess of the less expensive reactant to ensure that substantially all of the more expensive reactant is consumed in the reaction. The reaction will proceed at ambient temperature for most combinations of reactants, but for some combinations of reactants, variations from the initial to final reaction conditions may vary between about −25° C. and reflux temperature of the mixture depending on the reactivity of the reactants, the desired reaction time, the solvent being used, the molar proportions, and similar factors of concern to the chemist operating the process.

When the reaction has proceeded to substantial completion, the product (I) can be recovered from the reaction mixture by known procedures. For example, the reaction mixture can be evaporated, under vacuum, if desired, to remove solvent and other volatiles, leaving the product, often as an oil, mixed with a small amount of solvent and any unreacted or unvolatilized starting materials. This residual mixture can be taken up in a solvent such as ethyl ether, washed with salt solution such as saturated sodium bicarbonate solution and with water, separated from the aqueous phases and dried over a water absorbent such as sodium sulfate or magnesium sulfate and then evaporated to leave the more pure product as an oil or crystalline material. Addition of hydrochloric acid (hydrogen chloride gas) or other economical acid such as sulfuric, maleic, naphthalenesulfonic, p-toluenesulfonic, oxalic acids in a suitable solvent, such as diethyl ether or methanol, converts the oil product to the corresponding salt form which crystallizes more readily than the free amine form of the product. The amine salt products can be recrystallized from solvent mixtures such as $C_1$ to $C_3$-alkanol/di-$C_1$ to $C_3$-alkyl ether, e.g., methanol/diethyl ether, to give more easily handled crystalline forms of the product as the amine salts. Examples of such procedures are described in the detailed examples.

The trans-1,2-diamines (IIa), which can be used as starting materials to prepare compounds of this invention can be prepared by procedures known in the art. For example, amines of the formula

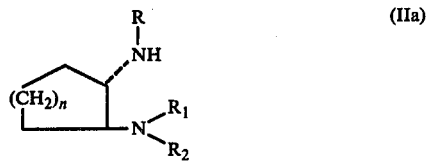  (IIa)

wherein R is $C_1$ to $C_3$-alkyl; and $R_1$ and $R_2$, as defined above, except that when $R_1$ and $R_2$ are taken separately, $R_1$ and $R_2$ are not hydrogen, benzyl or any hydrocarbon group with carbon to carbon unsaturation, can be prepared by reacting the respective 1,2-cycloalkane epoxide with the amine $HNR_1R_2$ wherein $R_1$ and $R_2$ are as defined immediately above to form the 2-aminocycloalkanol of the formula

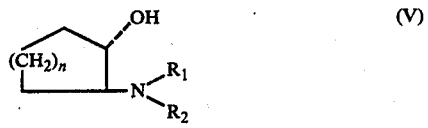  (V)

wherein n, $R_1$, and $R_2$ are as defined immediately above, and then reacting this aminocycloalkanol intermediate (V) first with a $C_1$ to $C_6$-alkanesulfonyl halide, e.g., with methanesulfonyl chloride, and then with a α-benzylamine of the formula $C_6H_5CH_2NHR$ where R is as generally defined above, to form a compound of the formula

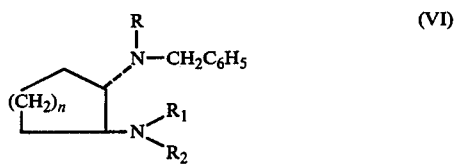  (VI)

wherein n, $R_1$ and $R_2$ are as defined immediately above, and then hydrogenolyzing this diamine (VI) with hydrogen in the presence of a palladium on charcoal catalyst and acid to remove the benzyl group and to form the trans-diamine starting material (IIa). Similarly, trans-1,2-cycloaliphatic amines IIa can be prepared by reacting a bicyclic aziridine of the formula

  (VII)

where R is hydrogen or $C_1$ to $C_3$-alkyl, with an amine of the formula $HNR_1R_2$ wherein $R_1$ and $R_2$, taken separately, are hydrogen, $C_1$ to $C_3$-alkyl, or when $R_1$ is hydrogen $R_2$ is $C_1$ to $C_6$-alkyl, —$CH_2CF_3$, $C_3$ to $C_6$-(allylic)alkenyl, $C_2$ to $C_5$-hydroxyalkyl, $C_3$ to $C_6$-cycloalkyl, $C_3$ to $C_4$-cycloalkylmethyl, phenyl-$C_1$ to $C_3$-alkyl or $R_1$ and $R_2$ taken together with the nitrogen to which they are bonded, complete a saturated monocyclic nitrogen heterocyclic ring containing only carbon and nitrogen ring atoms, from 3 to 5 ring carbon atoms, such saturated heterocyclic ring moieties having 3 to 4 ring carbon atoms permissively being substituted in the 3-position of the ring with hydroxy, $C_1$ to $C_3$-alkanoyloxy, $C_1$ to $C_3$ alkyloxy, and said saturated heterocyclic rings having five ring carbon atoms permissively being substituted in the 3- or 4-positions with hydroxy, $C_1$ to $C_3$-alkanoyloxy $C_1$ to $C_3$-alkyloxy respectively, to form the diamine starting material (IIa). This amine synthesis method is applicable whether the amino group in the 2-position of the saturated cycloaliphatic ring moiety is to be a tertiary, secondary or a primary amino group, and this method is imperative when this 2-amino ($-NR_1R_2$) group is to have attached thereto at least one $C_3$ to $C_6$-(allylic)alkenyl group.

The trans 1,2-cycloaliphatic diamine starting material (IIa) is then reacted with the aracyl imidazole (III) or with the acyl halide (IV) to form the trans product of this invention (Ia). For example, if it is desired to prepare a trans compound of formula I wherein $R_2$ is a $C_3$ to $C_6$-(allylic)alkenyl one process route which can be used would comprise (a) reacting an amine of the formula $HNR_1R_2$ where $R_1$ is as defined above when $R_2$ is a $C_3$ to $C_6$-(allylic)alkenyl with a bicyclic aziridine of formula VII, above, to form the trans diamine of the formula

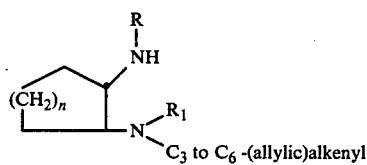

and then (b) react this trans-1,2-cycloaliphatic diamine (VIII) with the aracyl imidazole (III) or the acyl halide (IV) in an organic solvent for a time sufficient to form the trans compound of formula Ia wherein $R_2$ is the $C_3$ to $C_6$-(allylic)alkenyl group.

The cis-1,2-diamine starting materials (IIb) can be prepared by reacting an unsaturated cycloaliphatic amine of the formula

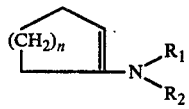

wherein n, $R_1$ and $R_2$ are as generally defined above, with an alkyl (preferably $C_1$ to $C_3$-alkyl) or benzyl chloroformate and then with hydrogen in the presence of catalyst, such as platinum oxide, to form the alkyl or benzyl 2-amino-1-cycloaliphatic carboxylate of the formula

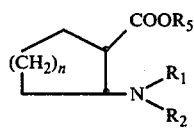

where $R_5$ is the alkyl or benzyl group from the chloroformate ester and n, $R_1$ and $R_2$ are as described above. This amino ester (X) can then be hydrolyzed with mineral acid or alkali metal base when $R_5$ is alkyl, or hydrogenolyzed in the presence of palladium on carbon catalyst when $R_5$ is benzyl, to form the amino-acid of the formula

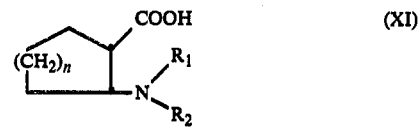

wherein n, $R_1$ and $R_2$ are as defined above.

In these structures the double heavy dots (•) at positions 1 and 2 of the cycloaliphatic ring denotes cis-stereoconfiguration of the substituents at the 1- and 2-positions to each other. One such dot denotes a trans configuration.

Electrophilic addition to enamines (e.g., IX) to give the 2-carboxy substituted enamines is known in the art; for example, A. G. Cook, ed., *Enamines: Synthesis, Structure and Reactions*, M. Dekker, New York, 1969.

This amino-acid (XI) can then be converted to the cis- diamine (IIb), by a known Curtius reaction (T. Curtius, J. Prakt. Chem., [2] 50, 274 (1894); see also *Merck Index*, Eighth Edition, (1968), (p. 1156), and can be used as a cis-starting material,

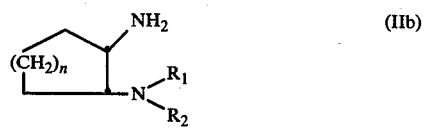

wherein n, $R_1$ and $R_2$ are as defined above.

The above unsaturated cycloaliphatic amine intermediates (IX) are prepared by reacting the corresponding cycloaliphatic ketone of the formula

with an amine of the formula $HNR_1R_2$ in the presence of an acid such as titanium tetrachloride. The use of titanium tetrachloride in the preparation of enamines has been described in *J. Organic Chemistry*, 32, 213 (1967).

When it is desired to prepare a cis-product containing a N-methyl group in the 1-position of the 1,2-cycloaliphatic diamine ($R = CH_3$) the cis- diamine starting material (IIb) is treated with an alkyl formate to form a compound of the formula

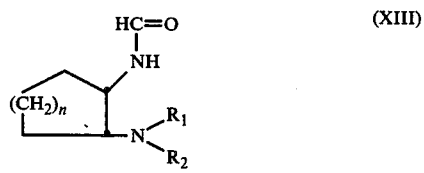

which compound XIII can then be reduced, e.g., with chemical reducing agents such as lithium aluminum hydride, to form the N-methylated cis-1,2-diamine of the formula XIVa

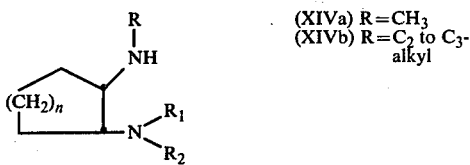

(XIVa) R=CH$_3$
(XIVb) R=C$_2$ to C$_3$-alkyl

The primary cis-1,2-diamine (IIb) and the secondary cis-1,2-diamine (XIVa) can then be treated according to the process of this invention which the aracyl imidazole (III) or with the acyl halide (IV) as described above to prepare cis- compounds (Ib) of this invention.

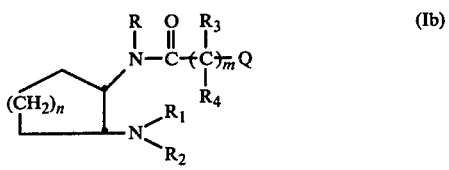

(Ib)

When the cis compounds (Ib) of this invention is to have an alkyl group other than methyl in the R position, the primary cis-1,2-diamine (IIb) can be reacted with an alkanoyl halide, e.g., with a C$_2$ to C$_3$-alkanoyl chloride or bromide, and then with a chemical reducing agent, e.g., lithium aluminum hydride, to form the secondary N-C$_2$ or C$_3$ alkyl cis-1,2-diamine starting material of the formula (XIVb) wherein the R group would be a higher alkyl group, preferably an ethyl or propyl group. Then this secondary N-C$_2$ or C$_3$-alkyl cis-1,2-diamine (XIVb) would be reacted with the aracyl imidazole (III) or the acyl halide (IV) to form the cis product (Ib) of this invention. When it is desired that the cis-product of this invention have C$_3$ to C$_6$-(allylic)alkenyl group in the R$_2$ position, the primary cis-1,2-diamine (IIb) with R$_2$ = benzyl (XV) is prepared from the ketone XII

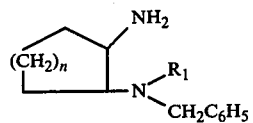

(XV)

by reacting with an N-benzyl-N-R$_1$ amine, as described above. This diamine (XV) is then hydrogenated in the presence of palladium on carbon catalyst to remove the benzyl group and form the cis-1,2-diamine of the formula

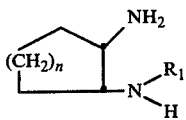

(XVI)

The cis-1,2-diamine (XVI) is then reacted with the selected aracyl imidazole (III) or acyl halide (IV) to form the cis-amide of the formula

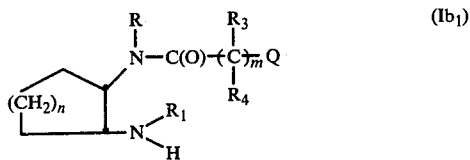

(Ib$_1$)

which amide (Ib$_1$) is also a useful analgesic in pharmaceutical product form, but which is primarily of interest for use as an intermediate to form the cis-products of this invention (Ib) wherein R$_2$ is an allylic C$_3$ to C$_6$-alkenyl group. For this purpose the intermediate product (Ib$_1$) is reacted with an allylic alkenyl halide, preferably the bromide or iodide, to form the cis-products of this invention (Ib) wherein R$_2$ is C$_3$ to C$_6$-(allylic)alkenyl.

Procedures for preparing the aracyl imidazoles (III) and acyl halide (IV) reactants used to form compounds of this invention are known in the art. See, for example, R. B. Wagner and H. D. Zook, *Synthetic Organic Chemistry*, 1953, John Wiley and Sons, Chapter 17, p. 546 et seq. The aracyl imidazole can be prepared in situ by reacting carbonyldiimidazole with the acid of the formula

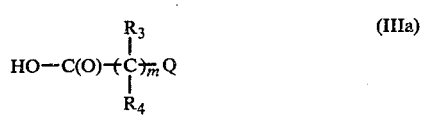

(IIIa)

in an organic solvent. Other carbodiimides such as dicyclohexylcarbodiimide can be used in place of the carbonyldiimidazole.

Acid addition salts can be prepared by reacting a Formula I free base with a stoichiometric amount of an acid, such as hydrogen chloride, hydrogen bromide, hydrogen iodide, sulfuric acid, phosphoric acid, acetic acid, lactic acid, citric acid, succinic acid, benzoic acid, salicyclic acid, pamoic acid, cyclohexanesulfamic acid, methanesulfonic, naphthalenesulfonic, p-toluenesulfonic, maleic, fumaric, oxalic acids and the like. The reaction can be carried out in aqueous or organic liquid solvent non-aqueous media such as diethyl ether, ethyl acetate, and the like. Non-aqueous media are preferred. When it is desired to obtain optically resolved products in crystalline form, it may be more convenient to form salts such as maleates, citrates or pamoates rather than the inorganic acid addition salts, such as the hydrochlorides. Also, whereas oxalic acid can be used to get the amino-amide product into a more easily handled solid form, it would preferably not be used as a pharmaceutically acceptable salt form of the amino-amide product.

Example of compounds within the scope of this invention include the cis- and trans- isomers of the following compounds:

N-2-[N'-methyl-N'-(2-phenylethyl)amino]cyclohexyl-N-methyl-2-(4-bromophenyl)acetamide;

N-[2-(N,N'-dimethylamino)cyclohexyl]-N-methyl-2-(4-trifluoromethylphenyl)acetamide;

N-[2-(N'-methyl-N'-cyclopropylmethylamino)cyclohexyl]-2-(2,4-dibromophenyl)acetamide maleate;

N-[2-(N'-allyl-N'-methylamino)cyclohexyl]-2-(2,4-dibromophenyl)acetamide;

N-[2-(N',N'-dimethylamino)cyclohexyl]-N-propyl-2-(3-methoxyphenyl)acetamide;

N-[2-(N',N'-dimethylamino)cyclohexyl]-2-(2,4,6-trimethylphenyl)acetamide;

N-[2-(N-pyrrolidinyl)cyclohexyl]-N-methyl-2-(4-bromophenyl)acetamide;

N-[2-(N',N'-dimethylamino)cyclohexyl]-N-methyl-2-(4-azidophenyl)acetamide;

N-[2-(N',N'-dimethylamino)cyclohexyl]-N-methyl-2-(3,4-dichlorophenyl)acetamide;

N-[2-(N',N'-dimethylamino)cyclohexyl]-N-methyl-2-(4-methoxyphenyl)acetamide;

N-[2-(N',N'-dimethylamino)cyclohexyl]-N-methyl-2-(4-chlorophenyl)propionamide;

N-[2-(N',N'-dimethylamino)cyclohexyl]-N-methyl-2-(2,4,6-trimethylphenyl)acetamide;

N-[2-(N',N'-dimethylamino)cyclohexyl]-N-methyl-2-(4-chlorophenyl]acetamide;

N-[2-(N',N'-dimethylamino)cyclohexyl]-N-methyl-2-(2-naphthyl)acetamide;

N-[2-(N',N'-dimethylamino)cyclohexyl]-2-(2-naphthyl)acetamide;

N-[2-(N',N'-dimethylamino)cyclohexyl]-2-(1-naphthyl)acetamide;

N-[2-(N'-methyl-N'-benzylamino)cycloheptyl]-N-ethyl-2-(4-bromophenyl)acetamide;

N-[2-(N',N'-dimethylamino)cyclooctyl]-N-methyl-2-(4-bromophenyl)acetamide;

N-[2-(N',N'-di-n-propylamino)cyclodecyl]-N-methyl-2-(4-azidophenyl)propionamide;

N-[2-(1-azetidinyl)cyclononyl]]-N-methyl-2-(3,4-difluorophenyl)acetamide;

1-(4-methoxyphenyl)-1-{N-[2-(N'-3-hydroxypropyl-N'-methyl)cyclopentyl]-N-methyl}-cyclopropanecarboxamide N-[2-(N-cyclopropyl-N-methylamino)cyclohexyl]-2-(4-azidophenyl)acetamide;

N-[2-(3-acetoxy-1-pyrrolidinyl)cyclohexyl]-N-methyl-2-(3,4-dichlorophenyl)acetamide;

N-[2-(N-pyrrolidinyl)cyclohexyl]-N-methyl-2-(3,4-dichlorophenyl)acetamide;

N-[2-(3-hydroxypyrrolidinyl)cyclohexyl]-N-methyl-2-(3,4-dichlorophenyl)acetamide;

N-[2-[N'-(2-hydroxyethyl)-N'-methylamino]cyclohexyl]-N-methyl-2-(4-bromophenyl)acetamide;

N-[2-(N'-butyl-N'-methylamino)cyclopentyl]-N-methyl-2-(3,4-dichlorophenyl)acetamide;

N-[2-[N'-(3-hydroxy-1-azetidinyl]cyclohexyl]methyl-2-(3,4-dichlorophenyl)acetamide;

N-[2-(N',N'-diethylamino)cyclohexyl]-N-methyl-2-(3,4-dichlorophenyl)acetamide;

N-[2-(N'-pyrrolidinyl)cyclohexyl]-N-methyl-2-(3,4-dichlorophenyl)propionamide;

N-[2-(N',N'-di-n-propyllamino)cyclohexyl]-N-methyl-2-(2,4,5-trichlorophenyl)acetamide;

N-[2-(4-methyl-N-piperazinyl)cyclohexyl]-N-methyl-2-(4-bromophenyl)acetamide;

N-[2-(4-methyl-1-piperazinyl)cyclopentyl]-2-(3,4-dichlorophenyl)acetamide;

N-[2-(N,N-dimethylamino)cyclohexyl]-2-(3,4-dichlorophenyl)acetamide;

N-[2-N,N-dimethylamino)cyclohexyl]-2-(3,4-dibromophenyl]acetamide;

N-[2-(N-piperidino)cycloheptyl]-N-ethyl-2-(3,4-difluorophenyl)acetamide;

N-[2-[N-methyl-N-(2-hydroxyethyl)cyclohexyl]]-3-(2,4,5-trichlorophenyl)propionamide;

N-[2-(N'-methyl-N'-cyclopropylamino)cyclopentyl]-4-(3,4-dichlorophenyl)butyramide;

N-[2-(N'-methyl-N'-cyclobutylmethylamino)cyclohexyl]-N-methyl-2-(4-azidophenyl)propionamide;

N-[2-(N-piperidinyl)cyclopentyl]-N-methyl-2-(4-biphenyl-1-yl)acetamide, and the like and the pharmaceutically acceptable salts thereof.

This invention also relates to compositions containing a formula I compound as an active ingredient in a pharmaceutical carrier. The compositions are useful in pharmaceutical dosage unit forms of the formula I compounds for local (topical) and systemic administration (oral, rectal and parenteral administration form) in therapy for treating and alleviating pain in humans and valuable animals, including dogs, cats and other commercially valuable and domestic animals.

The term "dosage unit form" as used in this specification and in the claims refers to physically discrete units suitable as unitary dosages for mammalian subjects, each unit containing a predetermined quantity of the essential active ingredient compound of this invention calculated to produce the desired effect, in combination with the required pharmaceutical means which adapt the said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of these amino-amide active ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exits. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg. of the essential active ingredient per dosage unit form, which as aforesaid may be in the form of a semi-solid or solid topical, oral, or rectal preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain analgesic and narcotic antagonist effects within the aforesaid effective non-toxic range. Expressed otherwise, when used systemically, an amount of the essential active ingredient is provided to a recipient within a range from about 0.01 mg. per kg. to about 5 mg. per kg. of body weight of the recipient.

Preferred dosages for most applications are 0.05 to 2.0 mg. per kg. of body weight. In a topical semi-solid ointment formulation the concentration of the active ingredient may be 0.1–10%, preferably 0.5–5% in a carrier, such as a pharmaceutical cream base.

The useful pharmaceutical dosages unit forms of these compounds in pharmaceutical formulations in preferably adapted for systemic administration to obtain analgesic and narcotic antagonist effects comprising an effective, non-toxic amount of a compound according to Formula I or as its pharmacologically acceptable salt.

Further the invention relates to methods of obtaining analgesic effects in mammals, for example, hu- and valuable warm-blooded animals such as dogs, cats, horses and other commercially valuable animals, by administering systemically to the mammals the aforesaid pharmaceutical dosage unit forms supplying an effective, non-toxic amount for analgesic and narcotic antagonist effects. These compounds have an advantage, to a greater extent, depending upon the particular compound, of having lower physical dependence liability than known analgesic compounds such as morphone and methadone, as shown by evaluation of representative compounds and those standard analgesic drug compounds in various pharmacological test procedures which measure relative degrees of analgesic and the physical dependence liability of the test compounds in standard laboratory test animals.

Representative examples of these formula I compounds, have $ED_{50}$ values ($\pm$ percent confidence limit) of less than about 75 mg/kg s.c. (subcutaneous administration) in standard laboratory animal analgesic tests such as the tail flick, pinch, and writhing tests, and the more potent of them have $ED_{50}$ values of less than 10 mg/kg (s.c.) in these tests, while at the same time giving quite high values (greater than 100 mg/kg s.c.) in the naloxone jumping test thus possessing only low to moderate apparent physical dependence liability as compared to commercial analgesics used as standards. The procedures used to determine these properties of these new compounds were essentially those of Way et al., (Way, E. L. et al., "Simultaneous Quantitative Assessment of Morphine Tolerance and Physical Dependence," J. Pharmacol. Exp. Ther., 167, pp. 1–8 (1969) and Saalens et al. (Saalens, J. K. et al., "The Mouse Jumping Test - A Simple Screening Method to Estimate the Physical Dependence Capacity of Analgesics," Arch. Int. Pharmacodyn., 190, pp. 213–218 (1971). Statistical effective doses ($ED_{50}$ values) and 95% confidence limits were calculated by the method of Spearman and Karber (Finney, D. J., "Statistical Methods in Biological Assay," Hafner Publ., (1952).

For example, representative preferred compounds of formula I give low analgesic $ED_{50}$ values (less than about 10 mg. of test compound/kg. of animal body weight, subcutaneous administration route) in standard laboratory animal tests while at the same time possessing quite high $ED_{50}$ values (greater than 250 mg/kg s.c.) in the naxolone jumping test, evidencing substantial freedom from apparent physical dependence liability. In contrast, known analgesic drugs such as morphine and methadone exhibit analgesic $ED_{50}$ values of less than 2 mg/kg., s.c., respectively, in these standard analgesic tail flick, pinch and writhing tests, but are known to have high apparent physical dependence liability effects, and this is confirmed by their (morphine and methadone) having relatively low naloxone jumping $ED_{50}$ values ranging from 12 to 30 mg/kg s.c. Although other representative compounds of this invention have analgesic potencies somewhat less than the preferred compounds (analgesic activity $ED_{50}$ values up to about 70 mg/kg s.c., in these standard tests) they still are characterized by having only low to moderate apparent physical dependence liability.

The discoveries made for the compounds described and claimed in this invention are believed to be unique and could not be predicted because some of the formula I compounds, but which have different substituents in the $R_1$ and $R_2$ position or only one substituent on the aryl ring in the X, Y or Z position when R is hydrogen showed very weak, if any, analgesic activity in the standard laboratory animal analgesic tests.

Examples of Preparations of Trans-Cycloaliphatic Diamine Starting Materials

Procedure I — Preparation of trans-N,N-dimethyl-1,2-cyclohexanediamine

A. trans-2-Methylaminocyclohexanol

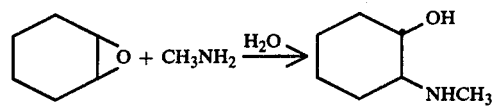

Cyclohexene oxide (196.28 g., 2 mole) is added during 30 min. to 40% aqueous methylamine (466 ml., 6 moles) with stirring. The temperature is from 25° to 27° during this addition. During the following 45 min. the temperature rises to 55° and is kept at 50° to 58° by occasional cooling. It is stirred at room temperature for 18 hr., then heated on the steam bath for 2 hrs., cooled and saturated with solid sodium hydroxide (NaOH). The mixture is extracted well with ether, the extract dried over magnesium sulfate ($MgSO_4$) and evaporated through a 9" Vigreux. Distillation at 13 mm gives 241.9 g. (97% yield) of the title compound b.p. 100°–101° nmr in $CDCl_3$ (100 MHz) is in accord; Mass spectrum $M^+$ 129.

This titled compound was reported by Mousseron et al., Bull. Soc. Chim, Fr., 850 (1947) by the reaction of cyclohexene oxide with methylamine for 2 hr. at 110°, b.p. 108°–109° (17 mm); HCl salt; m.p. 114°–115°.

B. N-Methyl-7-azabicyclo[4.1.0]heptane

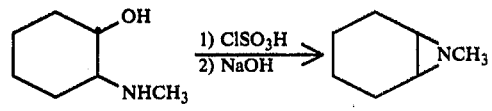

Chlorosulfonic acid (162.9 g., 1.4 mole) is added dropwise during 70 min. to a solution of trans-2-methylaminocyclohexanol (179.7 g., 1.39 mole) keeping the temperature at 5° to 10°. The thick mixture is stirred for 1.5 hr. at room temperature (raising the stirrer made agitation possible). Ether is decanted, and the product washed once with 300 ml. of ether by decantation. It is then cooled in ice, treated with a solution of 206 g. sodium hydroxide in 1 liter of water ($H_2O$)(cautiously at first). The mixture is then distilled, while adding $H_2O$ from a dropping funnel to keep the volume constant. About 600 ml. of distillate is collected during 4 hr. The distillate is saturated with solid sodium hydroxide and extracted with ether (8 × 100 ml.). The extract is dried (magnesium sulfate) and ether is distilled through a 9" glass helices column. The title product boils at 70°–72° (97 mm); 73 g. (47% yield).

nmr (nuclear magnetic resonance) in $CDCl_3$ (100 MHz) is in accord, Mass spectrum: $M^+111$; ir (infrared): CH 2960, 2940, 2860; N-alkyl 2760; C-N 1110; other 760 cm.$^{-1}$.

This compound was prepared before by T. Taguchi and M. Eto, JACS 80, 4076 (1958) in 37% yield by the procedure of Paris and Fanta for the synthesis of 7-azabicyclo[3.1.0]heptane; D. E. Paris and P. E. Fanta JACS 74, 3007 (1951) used carbon tetrachloride ($CCl_4$) in the above-mentioned procedure and steam-distilled the product after refluxing with alkali for 2 hours.

C. trans-N,N-Dimethyl-1,2-cyclohexanediamine

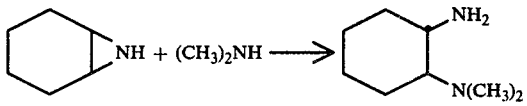

The starting 7-azabicyclo[4.1.0]heptane is best prepared according to the procedure of D. E. Paris and P. E. Fanta, JACS, 74, 3007 (1952) from trans-2-aminocyclohexanol with chlorosulfonic acid, followed by heating with aqueous sodium hydroxide. For the reaction with dimethylamine the procedure described in *Bull. Soc. Chim,* France, 382 (1956) was followed.

A mixture of 7-azabicyclo[4.1.0]heptane (12 g., 0.124 mole), 40 ml. of aqueous dimethylamine and 0.2 g. of ammonium chloride ($NH_4Cl$) is stirred and heated on the steam bath for 18 hr. and partly evaporated at room temperature in vacuo. Sodium hydroxide (NaOH) is added and the mixture extracted with ether. The extract is dried ($MgSO_4$) and evaporated. Distillation at 16 mm gives 8.1 g. (46% yield) of the titled compound as a colorless oil. nmr in $CDCl_3$ (100 MHz) is in accord. Mass spectrum: $M^+142$.

This compound is also prepared from trans-2-dimethylaminocyclohexanol by reaction with chlorosulfonic acid followed by ammonia, according to the procedure in *Helv. Chim. Acta,* 34, 1937 (1951).

Procedure II — Alternative Preparation of trans-N,N-dimethyl-1,2-cyclohexanediamine A. trans-2-dimethylaminocyclohexanol

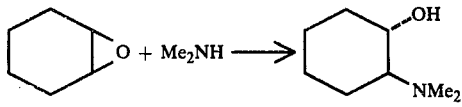

A mixture of cyclohexene oxide (196.28 g., 2 mole) and 40% aqueous dimethylamine (452 g., 4 mole) is stirred for two hours. An exothermic reaction occurs and the mixture is kept at 50°–55° by occasional cooling. It is then stirred at room temperature for 20 hr., heated at 95° for 1 hour and then for additional 1 hour with the condenser in the horizontal position. The mixture is cooled, extracted twice with ether (800 ml., 300 ml.), the ether extract washed with saturated salt solution, dried ($MgSO_4$), and evaporated. Distillation at 15 mm gives 265.1 g. (93% yield), b.p. 82°–83°; uv end absorption. ir: OH 3460; N-alkyl 2780; CH 1450; C-O/C-N 1300, 1270, 1185, 1120, 1085, 1060, 1035, 950, 875. nmr in $CDCl_3$ (100 MHz) confirms trans stereochemistry.

This compound was previously prepared from cyclohexene oxide and dimethylamine in benzene at room temperature for 14 days in 95% yield, b.p. 90° (20 mm): J. Chem. Soc., 4835 (1965); or in autoclave: C.A. 67, 63899 d. Rocz. Chem. 41, 541 (1967) b.p. 88° (14 mm); also Bull. Soc. Chim. France, 850 (1947): hydrochloride and resolution reported.

B. trans-N,N-dimethyl-1,2-cyclohexanediamine

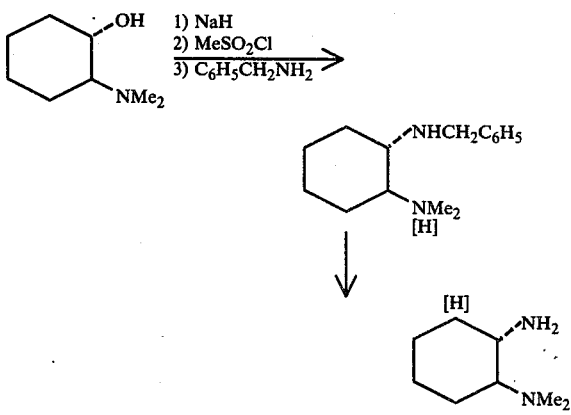

A solution of trans-2-dimethylaminocyclohexanol (58 g., 0.405 mole) prepared in Part A in 80 ml. of THF is added during 10 min. to a suspension of NaH (17.05 g., 0.405 mole of 57% dispersion in mineral oil) in 240 ml. of THF and the mixture is refluxed for 3 hours. It is cooled to 10° and methanesulfonyl chloride (46.39 g., 0.405 mole) added dropwise during 30 min., keeping the temperature below 10°. Benzylamine (86.79 g., 0.81 mole) is then added during 5 min., the solvent evaporated, and heating continued at 95° for 16 hr. NaOH (500 ml. of 20% solution) is added and the mixture heated at 95° for 1 hr., cooled, and extracted with ether (5 × 100 ml.). The ether solution is extracted with 10% HCl (6 × 100 ml.) and backwashed once with ether (discard). The acid extract is cooled, basified with 20% NaOH, and extracted with ether. The ether solution is washed with $H_2O$, saturated salt solution, dried ($MgSO_4$) and evaporated. Distillation at 0.4 mm gives 61 g. (65% yield) of N,N-dimethyl-N'-benzyl-1,2-cyclohexanediamine, b.p. 112°. It is identical by tlc to the sample prepared by the reaction of benzylamine with trans-2-chloro-1-dimethylaminocyclohexane (Procedure III).

A solution of the benzylamino compound is hydrogenated in two batches, each containing 30.5 g. (0.131 mole), 175 ml. EtOH, 3.4 g Pd-C and 56.5 g. (0.394 mole) of 70% $HClO_4$, at initial pressure of 51.5 p.s.i. for 19 hours. The two reduced batches are combined, filtered through Celite, and evaporated in vacuo at 45°. The residue is cooled in ice, basified with 40% KOH to pH 11. The resulting thick suspension is extracted with ether (5 × 200 ml.), the ether extract dried (MgSO₄) and evaporated through a 9" Vigreux. The residue is distilled at 13 mm to give 32.5 g. (87% yield), b.p. 77°–78.5°. ir and nmr are identical to those of the sample prepared by the reaction of 7-azabicyclo[4.1.0]heptane with dimethylamine (Procedure I, Part C).

Procedure III — Third Alternative Procedure for the Preparation of trans-N',N'-dimethyl-1,2-cyclohexanediamine A. trans-N'-Benzyl-N,N-dimethyl-1,2-cyclohexanediamine, p-toluenesulfonate (1:2)

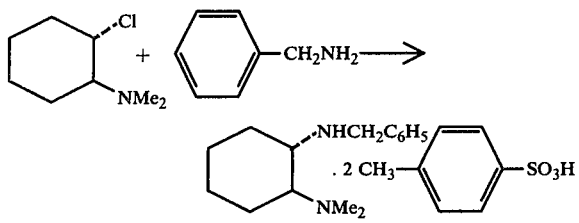

A mixture of trans 1-chloro-2-dimethylaminocyclohexane (56 g., 0.346 mole) and benzylamine (74.15 g., 0.692 mole) is heated at 95° for 17 hr. While still hot, it is poured into a solution of 85 ml. of conc. HCl and 425 ml. of H₂O, cooled, and extracted with ether (discard ether). The acidic solution is cooled in ice, basified with 40% NaOH, and extracted with ether. The ether extract is washed with H₂O, saturated salt solution, dried (MgSO₄) and evaporated. Distillation at 0.3 mm. gave 35.17 g. (44% yield). b.p. 114°–116°. uv:sh 209 nm (ε 11,100); λmax 247 (430); 252 (418); 258 (386); 264 (263); sh 267 (165); sh 278 (49); sh 288 (33). ir:NH 3290; =CH 3020; CH 2920, 2850, 2820; N-alkyl 2780; C = C/NH def. 1600, 1585, 1495, 1455; C-N 1030; aromatic 745, 735, 700. nmr in CDCl₃ is in accord. Mass spectrum M⁺282(small).

The salt is prepared with 2 moles of p-TSA in ether and crystallized from MeOH-ether, m.p. 158°–159.5°. uv:γmax 211 nm (ε 22,750); 219 (24,050); sh 222 (23,900); sh 252 (502); 256 (640); 261 (686); 267 (496); sh 271 (248). ir:N⁺H 3110-2600; N⁺H₂/C=C 1590, 1520, 1495; SO₃-/C-N/other 2235, 1220, 1170, 1150, 1120, 1030, 1005, 685; aromatic 820, 750, 700. nmr in D₂O (100 MHz) is in accord. Mass spectrum M⁺232.

Anal. Calcd. for C₁₅H₂₄N₂.2pTSA C, 60.39; H, 6.99; N, 4.86; S, 11.12.

Found: C, 60.39; H, 7.13; N, 4.79; S, 11.28.

B. trans-N',N'-dimethyl-1,2-cyclohexanediamine

The p-toluenesulfonate salt from part A (above) is basified with aq. NaOH to give the free diamine base as an oil. A solution of this oil is hydrogenated over 10% Pd-C and 70% NClO₄ and further treated as in Procedure VII to give the title diamine.

Procedure IV — trans-N,N'-dimethyl-N-allyl-1,2-cyclohexanediamine

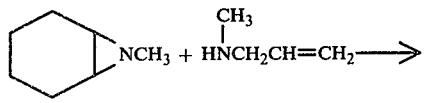

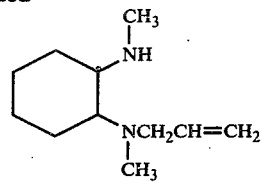

A mixture of N-methyl-azabicyclo[4.1.0]heptane (8.64 g., 0.078 mole), prepared as in Procedure I, Part B, N-allylmethylamine (11.05 g., 0.156 mole), 16.6 ml. of water, and 0.2 g. of ammonium chloride is stirred and heated in an oil bath maintained at 115°–117° for 16 hr. The mixture is cooled, saturated with solid sodium hydroxide and extracted well with ether. The ether extract is dried (MgSO₄), evaporated through a Vigreux column, and the titled product residue distilled at 13 mm; b.p. 104°–105°, 7.27 g. (51% yield).

nmr in CDCl₃ (100 MHz) is in accord. Mass spectrum: M⁺182 (v. small).

Procedure V — Preparation of trans-N,N,N'-trimethyl-1,2-cyclohexanediamine

A. trans-N-[2-(dimethylamino)cyclohexyl]formamide

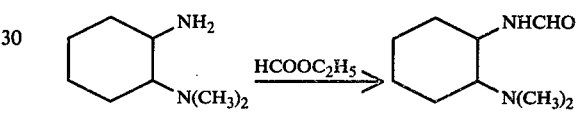

A solution of the diamine (5.12 g., 0.036 mole) and 100 ml. of ethyl formate (distilled over potassium carbonate) is refluxed for 17 hrs. and evaporated. The product is distilled at 0.1 mm, b.p. 104°, 5.2 g. (85% yield). ir:NH 3280, 3040, CH 2930, 2860, N-alkyl 2770, C=O 1670, amide 11 1540, other 1450, 1385 cm⁻¹; Nmr in CDCl₃ (100 MHz) is in accord. Mass spectrum: M⁺170.

B. N,N,N'-Trimethyl-1,2-cyclohexanediamine

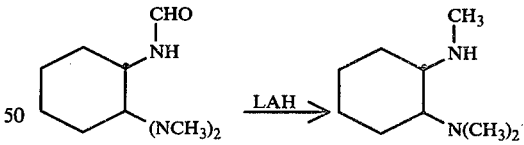

A solution of the N-formyl compound prepared in A (above)(4 g., 0.0235 mole) in 50 ml. of ether is added during 5 min. to a solution of lithium aluminum hydride (LAH)(4 g.) in 250 ml. of ethyl ether and refluxed 17 hrs. It is cooled in ice and decomposed by successive addition of 4 ml. of H₂O, 4 ml. of 15% sodium hydroxide in water, 12 ml. of H₂O, and stirring 1 hr. at room temperature, followed by filtration. The filter cake is washed with ether, and the ether removed by distillation through a Vigreux column. The title product residue distills at 14 mm. b.p. 86°–87°, 3 g. (82% yield). ir:NH 3680 (very weak), 3320; CH 2940, 2820; N-alkyl 2780; CH 1475, 1450, C-N/other 1270, 1155, 1145, 1125, 1060, 1045, 1005, 870, 805, 775 cm.⁻¹. Nmr in CDCl₃ (60 MHz) is in accord. Mass spectrum: M 156.

Procedure VI — Alternate Method for Preparing trans-N,N,N'-Trimethyl-1,2-cyclohexanediamine

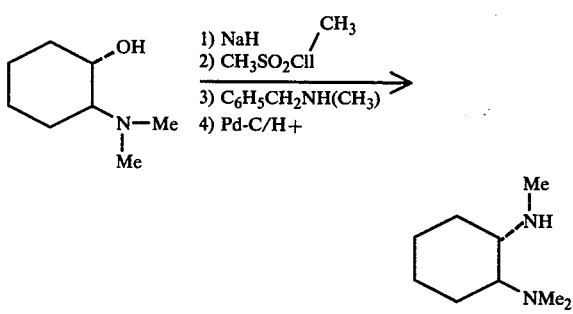

A solution of trans-2-dimethylaminocyclohexanol (61.1 g., 0.427 mole) prepared as in Procedure I, Part A, using dimethylamine instead of methylamine in 85 ml. of THF is added during 5 min. to a suspension of NaH (17.97 g., 0.427 mole of 57% dispersion in mineral oil) in 250 ml. of THF, and the mixture is heated at 95° for 2 hrs. It is cooled to 10° and treated dropwise with methanesulfonyl chloride (48.91 g., 0.427 mole) during 40 min. keeping the temperature at 15°. N-Methylbenzylamine (103.48 g., 0.854 mole distilled) is then added, THF is evaporated and heating is continued at 95° for 18 hr. The mixture is treated with 500 ml. of 20% NaOH, heated at 95°, cooled and extracted with ether (6 × 100 ml.). The ether solution is extracted with 10% HCl (6 × 100 ml.), backwashed with ether (discard ether), cooled, basified with 20% NaOH and extracted with ether. The ether extract is washed with $H_2O$, saturated salt solution, dried ($MgSO_4$) and evaporated to give 48.6 g. of crude N,N,N'-trimethyl-N'-benzyl-1,2-cyclohexanediamine as an oil. A solution of this oil (46.6 g.) is hydrogenated in two portions, each in 130 ml. of EtOH, with 2.6 g. of 10% Pd-C and 28.6 g. of 70% $HClO_4$ for 22 hrs. The mixture is filtered through Celite, the filtrate evaporated, cooled in ice, and basified with 40% KOH. The resulting thick suspension is extracted with ether (4 × 200 ml.), the ether extract dried ($MgSO_4$) and evaporated. The product boils at 87°–88° (16 min.). Vpc-mass spectrum showed that the first peak (3.4 min.) is N,N-dimethyl-1,2-cyclohexanediamine, and the second peak (4.1 min.) the desired N,N,N'-trimethyl-1,2-cyclohexanediamine.

A solution of the distillate (23.8 g.) in 50 ml. of ether is chromatographed on a column of Woelm neutral alumina (1200 g.) and eluted with 5% MeOH-ether. The center fractions (50 ml. each) gives 18.68 g. (the impurity is retained on the column). Distillation at 13 mm gives 17 g., b.p. 81°–82°. nmr in $CDCl_3$ (60 MHz) is identical to that of the compound prepared by Procedure III and V.

Procedure VII — A Third Method for Preparing trans-N,N',N'-trimethyl-1,2-cyclohexanediamine

A. trans-N-Benzyl-N-[2-(dimethylamino)cyclohexyl]formamide p-toluenesulfonate (1:1)

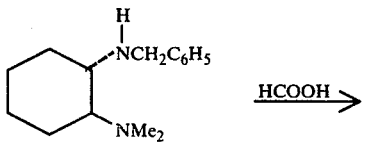

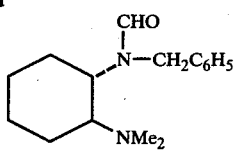

A solution of trans-N-benzyl-N',N'-dimethyl-1,2-cyclohexanediamine (9.29 g., 0.04 mole) prepared as in Procedure IV, but using benzylamine instead of benzylmethylamine, in 40 ml. of formic acid is refluxed 20 hr., and poured into 200 g. of ice. It is basified with 15% NaOH and extracted well with ether. The extract is washed with $H_2O$ and with saturated salt solution, is dried ($MgSO_4$) and evaporated. The residue is converted with 2 mole of p-TSA in ether. The resulting gum is crystallized from MeOH-ether to give 13.64 g. of title compound, m.p. 201°–201.5°. The analytical sample melts at 202°–203°. uv:sh 210 nm ($\epsilon$ 27,850); sh 222 (25,600); sh 227 (12,350); sh 243 (302); sh 248 (375); $\lambda$max 254 (472); 258 (556); 261 (562); 268 (399); sh 272 (175). ir:NH 2720, 2560; C=O 1670, 1650; C=C 1600, 1495; $SO_3$/other 1225, 1170, 1120, 1030, 1010, 815, 705, 685. nmr in $D_2O$ (100 MHz) is in accord. Mass spectrum $M^+260$.

Anal. Calcd. for $C_{16}H_{24}N_2O \cdot C_7H_7SO_3H$: C, 63.86; H, 7.46; N, 6.48; S, 7.41; Found: C, 64.04; H, 7.49; N, 6.34; S, 7.86.

The free base is prepared by basification of the ether-$H_2O$ suspension of the above salt and extraction with ether; it is a colorless oil.

B. trans-N-Benzyl-N,N',N'-trimethyl-1,2-cyclohexanediamine p-toluene sulfonate (1:1)

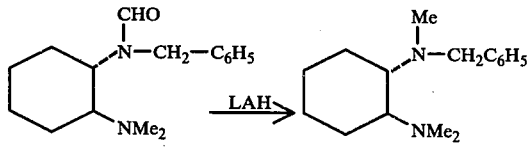

A solution of the free base from Part A (above) (5.7 g., 0.0219 mole) in 100 ml. of ether is added to a solution of LAH (5.7 g.) in 300 ml. of ether during 10 min., and the mixture is refluxed overnight. It is cooled in ice, and decomposed in succession with 5.7 ml. $H_2O$, 5.7 ml. of 15% NaOH and 17.1 ml of $H_2O$. The suspension is stirred at room temperature for 1 hr., filtered, and the cake washed with ether. The filtrate is dried ($MgSO_4$), and evaporated to give 5.6 g. of oil. The salt is prepared from 4.19 g. of the title amine base and 1 mole of p-toluenesulfonic acid monohydrate in ether. The resulting gum is crystallized from MeOH-ether; colorless needles of amine salt, 4.64 g., m.p. 143.5°–145°. uv:$\lambda$max 206 nm ($\epsilon$ 16,400); sh 221 (13,350); sh 226.5 (8,600); sh 247 (359); sh 252 (407); 257 (463); 261 (446); 267 (298); sh 271.5 (138) ir:$N^+H$ ~ broad; =CH 3060, 3040, 3020; N-alkyl 2810; C=C 1605, 1495; $SO_3^-$/other 1215, 1175, 1145, 1050, 1030, 1010, 815, 740, 695, 680. nmr in $D_2O$ (100 MHz) is in accord.

Anal. Calcd. for $C_{16}H_{26}N_2 \cdot CH_3C_6H_4SO_3H$: C, 65.99; H, 8.19; N, 6.69; S, 7.66; Found: C, 66.12; H, 8.04; N, 6.45; S, 7.69.

C. trans-N,N,'N'-trimethylcyclohexane-1,2-diamine

The p-toluenesulfonate salt from part B (above) is basified with aq. NaOH to give the free diamine base as an oil. A solution of this oil is hydrogenated over 10% Pd-C and 70% HClO$_4$ and further treated as in Procedure IX to give the titled diamine.

Examples of additional trans-cycloaliphatic diamine starting materials include the following compounds of the formula

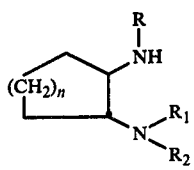

which are summarized in Table I below:

which can be used to prepare compounds of this invention.

Procedure VIII — Preparation of cis-N,N-dimethyl-1,2-cyclohexanediamine

A. 1-Dimethylaminocyclohex-1-ene

Titanium tetrachloride (237 g., 1.25 mole) is added in small portions over 4 hrs. to a solution of dimethyl amine (307 g., 6.82 mole) and cyclohexanone (223 g., 2.27 mole) in 600 ml. ether. Temperature is maintained below 5° during the addition. The mixture is stirred overnight at room temperature. The precipitate is collected and washed with ether. The ether is removed by distillation and the residual oil distilled at reduced pressure. After a small forerun, 243 g. (86% yield) of enamine (title compound) is obtained, b.p. 79°–80° (33 mm. Hg.) The nmr (CDCl$_3$) is in accord.

The use of titanium tetrachloride in the preparation of enamines has been described in *J. Org. Chem.*, 32, 213 (1967).

TABLE I
1,2-DIAMINE INTERMEDIATES

| NO. | n | N(R$_1$)(R$_2$) | R | PROCEDURE | MOLECULAR FORMULA | B.P. (° C/mm Hg.) |
|---|---|---|---|---|---|---|
| A | 2 | N—CH$_2$—cyclopropyl, CH$_3$ | CH$_3$ | IV | C$_{12}$H$_{24}$N$_2$ | 127–9° (13 mm) |
| B | 2 | N—CH$_2$—CH=CH$_2$, CH$_3$ | CH$_3$ | IV | C$_{11}$H$_{22}$N$_2$ | 104–5° (13 mm) |
| C | 2 | N—CH$_2$CH$_2$NCH$_2$CH$_2$ (CH$_3$) | CH$_3$ | IV(a) | C$_{12}$H$_{25}$N$_3$ | 143–5° (15 mm) |
| D | 2 | N—CH$_2$CH$_2$CH$_2$CH$_2$ | CH$_3$ | IV(a) | C$_{11}$H$_{22}$N$_2$ | 118–19° (13 mm) |
| E | 2 | N(CH$_2$CH$_2$OH)(CH$_3$) | CH$_3$ | IV | C$_{10}$H$_{22}$N$_2$O | 158–60° (14 mm) |
| F | 2 | N(n-C$_4$H$_9$)(CH$_3$) | CH$_3$ | IV(b) | C$_{12}$H$_{26}$N$_2$ | 118–20° (13 mm) |
| G | 2 | N-pyrrolidinyl-OH | CH$_3$ | IV | C$_{11}$H$_{22}$N$_2$O | 128–30° (0.1 mm) |
| H | 2 | N(CH$_3$)(CH$_3$) | H | I | C$_8$H$_{18}$N$_2$ | 78–79.5° (13 mm) |
| J | 2 | N(CH$_3$)(CH$_3$) | CH$_3$ | V | C$_9$H$_{20}$N$_2$ | 86–7° (14 mm) |
| K | 2 | N(C$_2$H$_5$)(C$_2$H$_5$) | CH$_3$ | V | C$_{11}$H$_{24}$N$_2$ | 104–5° (14 mm) |
| L | 3 | N-pyrrolidinyl | CH$_3$ | VI | C$_{13}$H$_{24}$N$_2$ | 148–151° (0.1 mm) |
| M | 3 | N(CH$_3$)(CH$_3$) | CH$_3$ | V | C$_9$H$_{19}$N$_2$ | 108–110° (17 mm) |
| N | 4 | N(CH$_3$)(CH$_3$) | CH$_3$ | V | C$_{10}$H$_{21}$N$_2$ | 113–115° (13 mm) |

Footnotes to Table I:
a. 4 eq. of amine
b. reaction ran in a sealed bomb
c. use pyrrolidine in place of methylamine The following preparations exemplify steps and procedures for preparing cis-1,2-diaminocycloalkanes

B. Ethyl ester of cis-2-(dimethylamino)cyclohexanecarboxylic acid

A solution of ethyl chloroformate (105 g., 0.97 mole) in 100 ml. benzene is added in 15 min. to a solution of the enamine (243 g., 1.94 mole) prepared in Part A in 1000 ml. benzene. The solution is refluxed overnight. The precipitate is collected and washed with benzene. The filtrate is concentrated to 1000 ml. and divided into four equal parts. Platinum oxide (5.0 g.) is added to each portion and each is hydrogenated at 50 p.s.i. until uptake of hydrogen ceases (1.13 mole total). The catalyst is removed by filtration and the solution evaporated. The residual oil is distilled at reduced pressure to give 128 g. (66% yield) amino ester, b.p. 69°–71°/0.3 mm; ir:CH 2940, 2860, 2820; N-alkyl 2760; C=O 1735; other 1655w, 1620w; CO 1175, 1166 cm$^{-1}$; nmr (CDCl$_3$) is in accord. Mass spectrum: M 199.

Anal. calcd. for $C_{11}H_{21}NO_2$: C, 66.29; H, 10.62; N, 7.03.

Found: C, 66.31; H, 11.05; N, 6.78.

C. cis-2-(N,N-dimethylamino)cyclohexanecarboxylic acid hydrochloride

A solution of the amino ester prepared in (B) (39.8 g., 0.30 mole) in 1500 ml. 10% HCl is refluxed for 19 hrs. The water is removed first by distillation, then at reduced pressure. The oil residue is treated with 500 ml. benzene and residual water removed by azeotropic distillation. The resulting solid is collected, washed with ether, and recrystallized from 350 ml. i-PrOH and 500 ml. ether; 50.9 g. (82% yield), m.p. 180°–181°; ir:acid OH/NH+ 2660, 2620, 2480, 2460; C=O 1720; CO/CH 1250, 1180, 1155; other 1000, 875, 715 cm$^{-1}$. Nmr (D$_2$O) is in accord. Mass spectrum: M+171.

Anal. calcd. for $C_9H_{17}NO_2 \cdot HCl$: C, 52.04; H, 8.73; N, 6.75; Cl, 17.07.

Found: C, 51.95; H, 8.77; N, 6.67; Cl, 16.92.

D. Curtius Reaction with cis-2-(N-dimethylamino)cyclohexanecarboxylic acid

A mixture of the amino acid prepared in Part C (31.2 g., 0.15 mole), diphenyl phosphoryl azide (41.3 g., 0.15 mole), and triethylamine (30.4 g., 0.30 mole) in 750 ml. benzene is refluxed with stirring for 1 hr. Benzyl alcohol (48.7 g., 0.45 mole) is added, and the mixture refluxed overnight. The mixture is extracted with 10% HCl. The extract is washed with ether, made basic with 40% KOH and extracted with ether. The organic layer is washed with water and saturated NaCl solution, dried, and evaporated. The residual oil is distilled to give 8.5 g. (20% yield) mixture of carbamate and benzyl ester, b.p. 130°–150°/0.1 mm. The nmr (CDCl$_3$) is consistent with a mixture of these two compounds.

E. cis-N,N-Dimethyl-1,2-cyclohexanediamine

The mixture obtained in Part D (above) (8.5 g.) is dissolved in 200 ml. ether, treated with 2.0 g. 10% Pd on carbon, and hydrogenated at 50 psi for 66 hrs. The mixture is filtered and the ether removed by distillation. The supernatant is removed by pipette from the precipitate which forms on standing, and is distilled at reduced pressure to give 1.65 g. of the title diamine, b.p. 70°/12 mm; ir:NH 3350, CH 2910, 2850; N-alkyl 2750; NH def 1590; CH 1465, 1440; CN/other 1215, 1160, 1045 cm$^{-1}$. Nmr (CDCl$_3$) is in accord. Mass spectrum: M+142. The diamine is thus separated from the precipitate which on workup is found to be the amino acid, cis-2-(N,N-dimethylamino)cyclohexanecarboxylic acid.

The following preparation exemplifies steps and procedures for preparing a cis-1,2-diaminocycloalkane of the formula

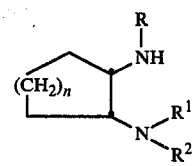

in which R is CH$_3$.

Procedure IX — Preparation of cis-N,N,N′-Trimethyl-1,2-cyclohexanediamine

A. cis-N-[2-(Dimethylamino)cyclohexyl]formamide

A solution of the diamine prepared above in Procedure IV Part E (1.65 g., 11.6 mmole) in 50 ml. of ethyl formate is refluxed overnight. The solution is evaporated to produce 2.07 g. (100% yield) of title formamide as a colorless oil. The material is used without purification. ir:NH 3300; CH 2910, 2850; N-alkyl 2760; C=O 1670; amide II 1535; other 1450, 1380, 1245, 1185, 1130, 1040, 980 cm$^{-1}$. Nmr is in accord. Mass spectrum: M+170.

B. cis-N,N,N′-trimethyl-1,2-cyclohexanediamine

A solution of the N-formamide obtained in step (A) (2.0 g., 11.3 mmole) in 20 ml. ether is added in 15 min. to a suspension of lithium aluminum hydride (LAH) (2.0 g.) in 100 ml. ether. The mixture is refluxed overnight. The excess LAH is decomposed by addition of 2 ml. water, 2 ml. 15% NaOH, and 6 ml. water. The precipitate is collected and washed with ether. The filtrate is dried (MgSO$_4$) and the ether removed by distillation. The residual oil is distilled at reduced pressure to give 1.40 g. (77% yield) title diamine, b.p. 70°/13 mm; ir:NH 3300; CH 2910, 2850; N-alkyl 2760; CH 1465, 1440; NH def/other 1365, 1335, 1240, 1165, 1140, 1110, 1090, 1040, 970, 890 cm$^{-1}$. Nmr (CDCl$_3$) is in accord. Mass spectrum: M+156.

This invention is further exemplified by the following detailed examples which can be used to prepare compounds of this invention, but they are not intended to limit the scope of the invention. All temperatures are in degrees Centigrade unless otherwise noted. For brevity, NaH means sodium hydride, DMF means N,N-dimethylformamide, THF means tetrahydrofuran, LAH means lithium aluminum hydride, MeI means methyl iodide, MeOH means methyl alcohol (methanol), CHCl$_3$ means chloroform, ether means diethyl ether, CH$_2$Cl$_2$ means methylene chloride, CDCl$_3$ means deuteriochloroform, HPLC means high pressure liquid chromatography, nmr means nuclear magnetic resonance, ir means infrared, and tlc means thin layer chromatography, pTSA means p-toluenesulfonic acid, D$_2$O means deuterated water (or deuterium oxide), DMSO means dimethylsulfoxide and VPC means vapor phase chromatography.

General Procedure A — for preparing amides of this invention using the carbonyl diimidazole method.

EXAMPLE 1(a)

N-Methyl-N-[2-(N',N'-dimethylamino)cyclohexyl]-2-(4-bromophenyl)acetamide hydrochloride

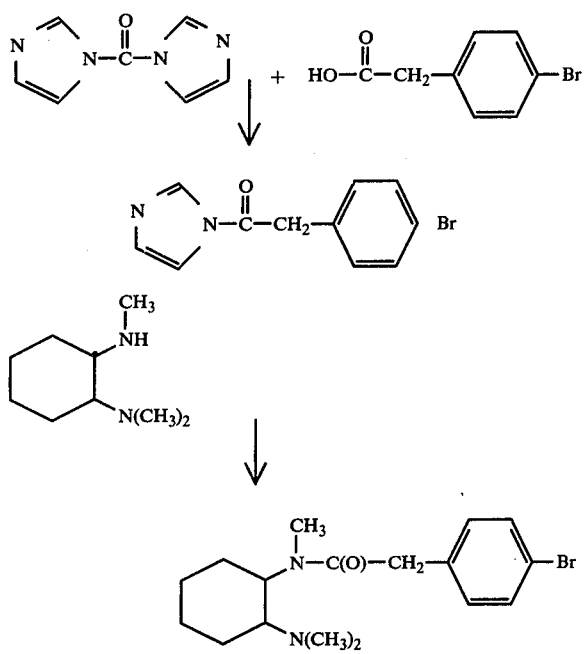

Carbonyl diimidazole (0.811 g., 5 mmole) is added to a solution of p-bromophenylacetic acid (0.106 g., 5 mmole) in 20 ml. dry THF and the solution stirred 1 hr. A solution of N,N,N'-trimethylcyclohexane-1,2-diamine (0.781 g., 5 mmole) is added during 10 min. and magnetically stirred 18 hrs. It is evaporated to dryness, taken up in 25 ml. ether, 20 ml. saturated aqueous sodium bicarbonate and the aqueous layer extracted once with ethyl ether. The combined ether extracts are washed with $H_2O$, saturated salt solution, dried over $MgSO_4$ and evaporated to give 1.8 g. of the title compound as an oil.

The crude oil is converted to the hydrochloride with ethereal HCl. Crystallization from methanol-ether gives the title compound as colorless crystalline needles, 78% yield, mp. 274°–275°. ir:NH 2640; C=O 1640; C=C 1595, 1490; other/aromatic 1425, 1400, 1165, 1015, 960, 810, 790 cm$^{-1}$. Mass spectrum: M$^+$352.

Anal. calcd. for $C_{17}H_{25}BrN_2O \cdot HCl$:
Calcd: C, 52.38; H, 6.72; Cl, 9.10; Br, 20.50; N, 7.19.

Found: C, 52.25; H, 6.79; Cl, 8.94; Br, 20.69; N, 7.29.
General Procedure B — for the preparation of amides of this invention via the acid chloride method.

EXAMPLE 1(b)

N-Methyl-N-[2-(N',N'-dimethylamino)cyclohexyl]-2-(4-bromophenyl)acetamide hydrochloride

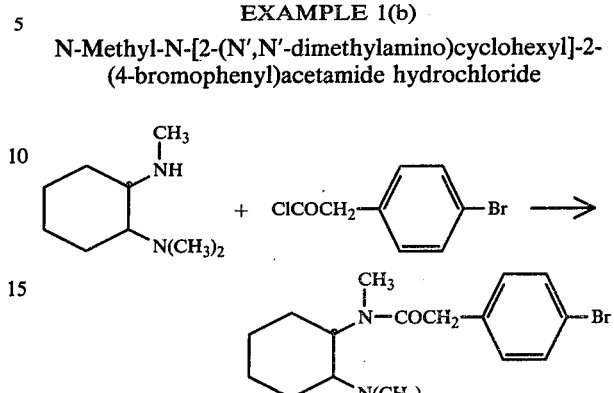

A solution of p-bromophenylacetyl chloride (1.17 g., 5 mmole) in 10 ml. of diethyl ether is added dropwise during 10 minutes to a solution of N,N,N'-trimethylcyclohexane-1,2-diamine (0.78 g., 5 mmole) in 50 ml. of diethyl ether containing triethylamine (0.505 g., 5 mmole), keeping the temperature at 20°–25°. The resulting suspension is stirred 18 hrs. Saturated aqueous sodium bicarbonate solution (25 ml.) is added, the ether layer separated, and the aqueous layer extracted once with ether. The combined ether extracts are washed with $H_2O$, saturated salt solution, dried ($MgSO_4$), and evaporated to give 1.8 g. of the title compound as an oil.

The crude oil is converted to the hydrochloride with ethereal HCl. This title amine salt is crystallized from MeOH-ether, mp. 274°–275° (60% yield). It is identical with the sample prepared in Example 1(a), as shown by mixed mp. and nmr comparison.

The following table (Table II) summarizes other trans-compounds of this invention, represented by the general formula

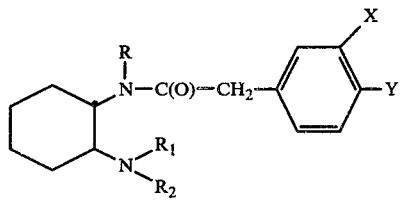

where R, —NR$_1$R$_2$, X and Y are as defined in Table II. z is hydrogen.

Table II

| Example Number | R$_1$R$_2$N— | R | X | Y | Salt | M.P. | Formula | Anal. Calc. | | Found | Starting Diamine From Table I |
|---|---|---|---|---|---|---|---|---|---|---|---|
| 2 | N(CH$_3$)$_2$ | CH$_3$ | H | 4-CF$_3$ | a | 228–230 | C$_{18}$H$_{25}$F$_3$N$_2$O . HCl 5H$_2$O | C, 55.74<br>H, 7.02<br>Cl 9.14<br>F 14.70<br>N 7.22 | C<br>H<br>Cl<br>F<br>N | 56.06<br>6.49<br>9.46<br>14.71<br>7.49 | J |
| 3 | —N—CH$_2$—◁<br>\|<br>CH$_3$ | CH$_3$ | H | 4-Br | b | 145–147.5 | C$_{20}$H$_{29}$BrN$_2$O . C$_4$H$_4$O$_4$ | C 56.58<br>H 6.53<br>Br 15.69<br>N 5.50 | C<br>H<br>Br<br>N | 56.94<br>6.51<br>15.34<br>5.75 | A |
| 4 | —N—CH$_2$CH=CH$_2$<br>\|<br>CH$_3$ | CH$_3$ | H | 4-Br | c | 162-3 | C$_{19}$H$_{27}$BrN$_2$O | C 56.61<br>H 6.40<br>Br 14.49<br>N 5.08<br>S 5.81 | C<br>H<br>Br<br>N<br>S | 56.99<br>6.40<br>14.42<br>5.08<br>5.74 | B |

Table II -continued

| Example Number | R₁R₂N— | R | X | Y | Salt | M.P. | Formula | Anal. Calc. | | Anal. Found | | Starting Diamine From Table I |
|---|---|---|---|---|---|---|---|---|---|---|---|---|
| 5 | N(CH$_3$)$_2$ | CH$_3$ | H | H | c | 200–201 | C$_{17}$H$_{26}$N$_2$O · CH$_3$C$_6$H$_4$SO$_3$H | C H N S | 64.54 7.67 6.27 7.18 | C H N S | 64.20 7.83 6.12 7.18 | J |
| 6 | N(CH$_3$)$_2$ | CH$_3$ | 3-OCH$_3$ | H | | 55–57.5 | C$_{18}$H$_{28}$N$_2$O$_2$ | C H N | 71.01 9.27 9.20 | C H N | 70.90 9.39 9.32 | J |
| 7 | N(CH$_3$)$_2$ | CH$_3$ | H | 4-CH$_3$ | a | 268–269 | C$_{18}$H$_{28}$N$_2$O · HCl | C H Cl N | 66.54 9.00 10.91 8.62 | C H Cl N | 66.54 8.95 10.97 8.56 | J |
| 8 | (N-methylpiperazinyl) | CH$_3$ | H | 4-Br | a | 257–9 dec. | C$_{20}$H$_{30}$BrN$_3$O 1.5 H$_2$O | C H Br Cl N | 47.25 6.94 15.72 13.95 8.26 | C H Br Cl N | 47.05 6.94 | C |
| 9 | (pyrrolidinyl) | CH$_3$ | H | 4-Br | a | 213–214 dec. | C$_{19}$H$_{27}$BrN$_2$O · 5 H$_2$O | C H Br Cl N | 53.71 6.88 18.81 8.35 6.60 | C H Br Cl N | 53.86 6.96 19.34 8.15 6.56 | D |
| 10 | N(CH$_3$)$_2$ | CH$_3$ | H | 4-N$_3$ | d | 174–176 dec. | C$_{17}$H$_{25}$N$_5$O · C$_2$H$_2$O$_4$ | C H N | 56.28 6.71 17.17 | C H N | 55.97 6.71 17.24 | J |
| 11 | —N(CH$_3$)$_2$ | CH$_3$ | 3-Cl | 4-Cl | c | 203–204 | C$_{17}$H$_{24}$Cl$_2$N$_2$O · CH$_3$C$_6$H$_4$SO$_3$H | C H Cl N S | 55.91 6.26 13.76 5.44 6.22 | C H Cl N S | 56.10 6.33 13.64 5.41 6.29 | J |
| 12 | —N(CH$_3$)$_2$ | CH$_3$ | H | 4-C$_6$H$_5$ | a | 242–243 | C$_{23}$H$_{30}$N$_2$O · HCl 0.5H$_2$O | C H Cl N | 69.76 8.15 8.95 7.08 | C H Cl N | 69.69 8.05 8.93 6.95 | J |
| 13 | —N(CH$_3$)$_2$ | CH$_3$ | H | 4-OCH$_3$ | a | 251–252 dec. | C$_{18}$H$_{28}$N$_2$O$_2$ · CHl | C H Cl N | 63.42 8.57 10.40 8.22 | C H Cl N | 63.02 8.52 10.58 8.08 | J |
| 14 | —N (pyrrolidinyl) | CH$_3$ | 3-Cl | 4-Cl | a | 205–206 | C$_{19}$H$_{28}$ClN$_2$O · HCl 0.5H$_2$O | C H Cl N | 55.01 6.80 25.64 6.75 | C H Cl N | 54.87 6.81 25.43 6.66 | D |
| 14A | —N (pyrrolidinyl) | CH$_3$ | 3-Cl | 4-Cl | a | 218–225 | C$_{19}$H$_{26}$ClN$_2$O · HCl | C H N Cl | 56.23 6.71 6.90 26.21 | C H N Cl | 56.15 6.88 6.81 26.22 | D |
| 15 | NCH$_2$CH$_2$OH \| CH$_3$ | CH$_3$ | 3-Cl | 4-Cl | a | 115 effer. | C$_{18}$H$_{26}$Cl$_2$N$_2$O$_2$ · HCl ½ H$_2$O | C H Cl N | 51.99 6.71 25.58 6.74 | C H Cl N | 52.03 6.90 25.16 6.50 | E |
| 16 | —N—CH$_2$CH$_2$CH$_2$CH$_3$ \| CH$_3$ | CH$_3$ | 3-Cl | 4-Cl | b | 140.5–142 | C$_{20}$H$_{30}$Cl$_2$N$_2$O · C$_4$H$_4$O$_4$ | C H Cl N | 57.48 6.83 14.14 5.59 | C H Cl N | 57.10 6.75 13.29 6.03 | F |
| 17 | —N (3-hydroxypyrrolidinyl) | CH$_3$ | 3-Cl | 4-Cl | a | 250–251 | C$_{19}$H$_{26}$Cl$_2$N$_2$O$_2$ · HCl | C H Cl N | 54.10 6.45 25.22 6.64 | C H Cl N | 54.15 6.49 25.33 6.72 | G |
| 18 | N—(CH$_2$CH$_3$)$_2$ | CH$_3$ | 3-Cl | 4-Cl | b | 160–161 | C$_{19}$H$_{28}$Cl$_2$N$_2$O · C$_4$H$_4$O$_4$ 0.5H$_2$O | C H Cl N | 55.64 6.70 14.28 5.64 | C H Cl N | 55.74 6.56 13.92 5.62 | K |

The following trans-compounds of the invention satisfy the general formula

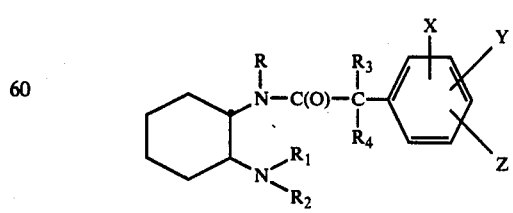

wherein R, —NR$_1$R$_2$, R$_3$, R$_4$, X, Y and Z are as defined in Table III.

TABLE III

| Ex. No. | M R₁R₂N— | R | R₃ | R₄ | X | Y | Z | Salt | M.P. | Formula | Anal. Calcd. | | Found | |
|---|---|---|---|---|---|---|---|---|---|---|---|---|---|---|
| 19 | N—CH₂CH₂CH₂CH₂ (2) | CH₃ | H | CH₃ | H | 3-Cl | 4-Cl | | 124–125 | C₂₀H₂₈Cl₂N₂O | C | 62.66 | C | 62.32 |
| | | | | | | | | | | | H | 7.36 | H | 7.38 |
| | | | | | | | | | | | Cl | 18.50 | Cl | 18.40 |
| | | | | | | | | | | | N | 7.31 | N | 7.04 |
| 20 | N(CH₃)₂ (3) | CH₃ | CH₃ | CH₃ | H | H | H | | 79.5–80.5 | C₁₉H₃₀N₂O | C | 75.45 | C | 74.97 |
| | | | | | | | | | | | H | 10.00 | H | 9.83 |
| | | | | | | | | | | | N | 9.26 | N | 9.21 |
| 21 | N(CH₃)₂ [isomer I] | CH₃ | H | CH₃ | H | H | 4-Cl | | 90–92 | C₁₈H₂₇ClN₂O | | | | |
| 22 | N(CH₃)₂ [isomer II] (3) | CH₃ | H | CH₃ | H | H | 4-Cl | | 93–94 | C₁₈H₂₇ClN₂O | C | 66.95 | C | 66.83 |
| | | | | | | | | | | | H | 8.43 | H | 8.36 |
| | | | | | | | | | | | Cl | 10.98 | Cl | 11.02 |
| | | | | | | | | | | | N | 8.68 | N | 8.51 |
| 23 | N(CH₃)₂ | H | H | H | 2-CH₃ | 4-CH₃ | 6-CH₃ | a | 279–280 dec. | C₂₀H₃₂N₂O · HCl | C | 68.06 | C | 67.88 |
| | | | | | | | | | | | H | 9.42 | H | 9.66 |
| | | | | | | | | | | | Cl | 10.05 | Cl | 10.27 |
| | | | | | | | | | | | N | 7.94 | N | 7.92 |
| 24 | N(CH₃)₂ | H | H | H | 3-Cl | 4-Cl | H | | 129–128 | C₁₆H₂₂Cl₂N₂O | C | 58.36 | C | 58.22 |
| | | | | | | | | | | | H | 6.74 | H | 6.90 |
| | | | | | | | | | | | Cl | 21.54 | Cl | 21.75 |
| | | | | | | | | | | | N | 8.51 | N | 8.70 |

FOOTNOTES FOR TABLES II AND III:
(a) - hydrochloride
(b) - maleate
(c) - tosylate
(d) - oxalate
(1) - Crystallization solvent is methanol/ethyl ether (50:50 v/v)
(2) - Ethyl ether crystallization solvent
(3) - Petroleum ether crystallization solvent The following compounds of the invention (Table IV) exemplify the compounds of the invention having:
(a) R₃ and R₄ taken together with the carbon to which they are bonded denoting a cyclopropylene ring (Example 25).
(b) The compounds of the invention wherein Q is 1-naphthyl or 2-naphthyl (Examples 26 and 27).
(c) The compounds of the invention wherein n is more than 1 or 2. (Examples 28 to 30).

TABLE IV

| Structure | Ex. No. | Salt | M.P. | Formula | Anal. Calcd. | | | Found | | |
|---|---|---|---|---|---|---|---|---|---|---|
| [cyclohexyl-N(CH₃)-CO-cyclopropyl-C₆H₄-Cl; N(CH₃)₂] | 25 | | 82.3 | C₁₉H₂₇ClN₂O | C, 68.14; | H, 8.13; | | C, 68.03; | H, 8.21 | |
| | | | | | Cl, 10.59; | N, 8.37 | | Cl, 10.56; | N, 8.39 | |
| [cyclohexyl-N(CH₃)-CO-CH₂-2-naphthyl; N(CH₃)₂] | 26 | a | 227–8 | C₂₁H₂₈N₂O · HCl · 0.5H₂O | C, 68.17; | H, 8.17; | | C, 68.02; | H, 8.06 | |
| | | | | | Cl, 9.59 | N, 7.57 | | Cl, 9.82; | N, 7.42 | |
| [cyclohexyl-N(CH₃)-COCH₂-1-naphthyl; N(CH₃)₂] | 27 | a | 251–2 | C₂₁H₂₈N₂O · HCl · ¼H₂O | C, 68.73; | H, 8.15; | | C, 68.85; | H, 8.04 | |
| | | | | | Cl, 9.66; | N, 7.64 | | Cl, 9.85; | N, 7.60 | |
| [cycloheptyl(7)-N(CH₃)-COCH₂-C₆H₄-Br; N(CH₃)₂] | 28 | c | 174–5 | C₁₈H₂₇BrN₂O · C₄H₄O₄ | C, 54.66; | H, 6.46; | | C, 54.61; | H, 6.58 | |
| | | | | | Br, 16.53; | N, 5.80 | | Br, 16.11; | N, 5.86 | |
| [cyclooctyl(8)-N(CH₃)-COCH₂-C₆H₄-Br; N(CH₃)₂] | 29 | b | 191–2 | C₁₉H₂₈BrN₂O · C₁₀H₈SO₃ | C, 59.07; | H, 6.33; | | C, 58.97; | H, 6.40 | |
| | | | | | Br, 13.55; | N, 4.75 | | Br, 13.26; | N, 4.93 | |
| | | | | | S, 5.44 | | | S, 5.25 | | |
| [cycloheptyl-N(CH₃)-CO-CH₂-C₆H₃(Cl)₂; pyrrolidinyl] | 30 | a | 134–6 | C₂₀H₂₈Cl₂N₂O · HCl · ¼H₂O | C, 56.01; | H, 7.05; | | C, 56.07; | H, 6.98 | |
| | | | | | Cl, 24.80; | N, 6.53 | | Cl, 24.96; | N, 6.36 | |

Footnotes: Table IV -
(a) hydrochloride
(b) napsylate
(c) maleate

EXAMPLE 14 and 14A

Preparation of trans-2-(3,4-dichlorophenyl)-N-methyl-N-[2-(1-pyrrolidinyl)cyclohexyl] acetamide hydrochloride A 5.62 g. (0.0274 mole) portion of 3,4-dichlorophenylacetic acid is dissolved in 100 ml. of tetrahydrofuran (THF). To this solution is added 4.4 g. 4.4 g. (0.0274 mole) of 1,1'-carbonyldiimidazole (CDI) and the reaction mixture stirred for 2 hours at room temperature. Then 5.0 g. (0.027 mole) of trans-2-(N-pyrrolidinyl)cyclohexyl-N-methylamine in 25 ml. of the THF is added and the resulting mixture stirred for 20 hours at room temperature. The mixture is evaporated to dryness, the residue is taken up in ethyl ether and mixed with a saturated aqueous sodium bicarbonate solution. The ether layer is separated from the aqueous layer, washed well with water and dried over magnesium sulfate ($MgSO_4$) to give a residue which is dissolved in methanol. To the resulting methanol solution is added 1N ethereal hydrogen chloride solution (hydrogen chloride in diethyl ether) to lower the pH of the mixture to less than 7; then diethyl ether is added to the point of cloudiness. The product crystalline hydrochloride salt (solvate hemihydrate) is collected in 84.5% yield (9.4 g.), m.p. 205°–206° C. See Table II for its elemental analysis. (Example 14); drying the solvate for 18 hr. at 65° and 0.1 mm Hg. gives the non-solvated hydrochloride salt. See Table II for elemental analysis (Example 14A)

EXAMPLE 14(b)

A 5 gr. portion of trans-2-(3,4-dichlorophenyl)-N-methyl-N-[2-(1-pyrrolidinyl)cyclohexyl]acetamide hydrochloride (Example 14) was converted to its free base form with 20% sodium hydroxide aqueous solution, and the mixture was extracted with chloroform. The chloroform extracts were dried with anhydrous magnesium sulfate and evaporated to dryness to leave 4.3 g. of colorless amino-amide oil which was then converted to the maleic acid salt as follows:

The 4.3 g. of amino-amide oil was dissolved in methanol and 1.35 g. (0.0116 mole) of maleic acid in ether was added. Additional ether was introduced to the solution to the point of cloudiness; on standing crystallization occurred to give 4.6 g. of the trans 2-(3,4-dichlorophenyl)-N-methyl-N-[2-(1-pyrrolidinyl)cyclohexyl]acetamide maleate salt (colorless rods), m.p., 191°–192°. The crystals were dried at 65° c. (0.1 mm, 18 hrs.). The ir spectrum was consistent with the named structure.

Anal. $C_{19}H_{26}N_2OCl_2 \cdot C_4H_4O_4$

Calcd.: C, 56.91; H, 6.23; N, 5.77; Cl, 14.61.
Found: C, 56.92; H, 6.35; N, 5.72; Cl, 14.80.

The maleate salt form of some of these amino-amide compounds has been found particularly useful for resolving the d- and l- isomers of these compounds, for further specific study in the pharmacology of these drug compounds.

Preliminary pharmacological testing of the separated trans-d- and trans-l-isomers of this compound, trans-2-(3,4-dichlorophenyl)-N-methyl-N-[2-(1-pyrrolidinyl)-cyclohexyl]acetamide maleate, indicates that the analgesic activity of these compounds resides in the l-isomer, but analgesic activity is also shown by the trans-dl-isomer mixtures thereof, and such mixtures are included within this invention.

EXAMPLE 31

Trans-2-(3,4-dichlorophenyl)-N-methyl-N-[2-(3-acetoxy-1-pyrrolidinyl)cyclohexyl]acetamide hydrochloride hemihydrate Following the procedure of Example 14 but substituting trans-N-[2-(3-hydroxyl-1-pyrrolidinyl)cyclohexyl]-N-methylamine for the trans-2-(N-pyrrolidinyl)cyclohexyl-N-methylamine there is obtained trans-2(3,4-dichlorophenyl)-N-methyl-N-[2-(3-hydroxy-1-pyrrolidinyl)cyclohexyl]acetamide as the hydrochloride.

Then, in a nitrogen atmosphere, a mixture of 0.9 g. (0.002 mole) of the trans-2-(3,4-dichlorophenyl)-N-methyl-N-[2-(3-hydroxy-1-pyrrolidinyl)cyclohexyl]acetamide and 5 ml. of acetic anhydride is heated on a steam bath for 4 hours. Then 10 ml. of water is added and the mixture is further heated on the steam bath for 30 minutes. The resulting solution is cooled in ice and basified to pH 7-8 by addition of solid sodium bicarbonate. This resulting reaction mixture is extracted well with diethyl ether, the ether extracts are combined and washed well with water and saturated aqueous sodium chloride solution, dried over $MgSO_4$ and evaporated to dryness. A brown oil (0.562 g.) is obtained. This oil is converted to the hydrochloride salt in ether with ethereal HCl. Crystallization of the titled compound from a methanol-diethyl ether mixture gives 0.325 g. of off-white needles, m.p. 161°–162° C. The mass spectrum analysis shows an $M^+ 426$ ion.

Anal. for $C_{21}H_{28}Cl_2N_2O_3 \cdot HCl \cdot \frac{1}{2}H_2O$:
Calcd: C, 53.24; H, 6.40; Cl, 22.50; N, 5.93.
Found: C, 53.23; H, 6.25; Cl, 22.54; N, 5.92.

EXAMPLE 32

Cis-2-(3,4-dichlorophenyl)-N-methyl-[2-(1-pyrrolidinyl)cyclohexyl]acetamide

Following the procedure of Example 14 but substituting cis-1-N-methylamino-2-(1-pyrrolidinyl)cyclohexane prepared from cyclohexanone and pyrrolidine according to Procedures IV and V for the trans-2-(1-pyrrolidinyl)cyclohexyl-N-methylamine there is obtained the titled compound, which can be converted to its hydrochloride as in Example 14.

If desired the formula I compounds of this invention can be resolved into their respective d- and l-optical isomers by methods known in the art. In this case, the optical resolution can be done by at least two different routes. The resolving agents by either route are any of the known resolving agents such as optically active camphorsulfonic acid, bis-p-toluyltartaric acid, tartaric acid, and diacetyl tartaric acid which are commercially available and which are commonly used for resolution of amines (bases), as for example in Organic Syntheses, Coll. Vol. V., p. 932 (1973), resolution of d-(+) and 1-(−)-α-phenylethylamine with (+)-tartaric acid.

By the first method for resolving the compounds of this invention, for example, one of the amino amide compounds can be converted into its optically active diastereomeric salts by reaction with an optically active acid-examples mentioned above - in a manner standard in the isomer resolution art. These diastereomeric salts can then be separated by conventional means such as differential crystallization. Diastereomeric salts have different crystallization properties, which are taken advantage of in this separation. On neutralization of each diastereomeric salt with aqueous base the corresponding optically active enantiomers of the free amino amide can be obtained, each of which can subsequently and separately be converted as previously described in the examples to the desired acid addition salt.

By the second method, which in the case of some of these compounds is preferred, the formula I compounds can be made into their respective d- and l-isomers, by first resolving each cis- or trans-1,2-cycloaliphatic unsymmetrically substituted diamine into its respective d- and l-isomers by treatment with the resolving agent, crystallization, separation and regeneration of the respective trans-d-diamine, trans--diamine, or the cis-d-diamine and cis-l-diamine, and then reacting the respective resolved diamine starting material with the desired aracyl imidazole (III) or the acyl halide (IV) to form the respective cis or trans, d- or l- compound of formula I, which can then be converted to any desired pharmaceutically acceptable acid addition salt by procedures exemplified above.

EXAMPLE 33

Part A - Preparation of trans- d and l N-methyl-N-[2-(1-pyrrolidinyl)cyclohexyl]amine hydrochloride Di-p-toluyl-d-tartaric acid is dissolved in 100 ml. of methanol; this solution is added to a solution of trans - N-methyl-N-[2-(1- pyrrolidinyl)cyclohexyl]amine (4 g., 0.022 mole) in 100 ml. of methanol and the combined mixture is allowed to stand for 50 min. to crytallize. The suspension is filtered. The residue is washed with methanol and dried at 50° to give 6.01 g. of solid A (m.p. 194°–196°). Filtrate saved. One-half gram of solid A (acid addition salt) is converted to the free base with 20% NaOH in water and is then extracted into chloroform. The organic phase is dried over MgSO4, evaporated to dryness and converted to the hydrochloride salt in ethereal HCl. Recrystallization from CH3OH gives 95 mg. of colorless crystals (m.p. 236°–239°) of d-diamine hydrochloride $[\alpha]_D^{22°}$ +17° (C=16.52 mg/2ml chloroform).

Further refinements in the isolation of optically pure d amine hydrochloride: The remaining 5.5 g. of solid A is dissolved in 600 ml. CH3OH, concentrated to 200 ml. and the concentrate is set to crystallize overnight. 3.7 g. of solid is collected (m.p. 197°–198°). One-half gram of this solid is converted to the free base with 20% NaOH/CHCl3, the organic layer is washed with water and saturated sodium chloride solution, dried over MgSO4 and evaporated to dryness. Conversion to the hydrochloride salt in etheral HCl and crystallization from CH3OH gives colorless needles of the trans-s-diamine HCl, which are dried at 50° in vacuo (m.p. 247.5°–248.5°) $[\alpha]_D^{22°}$ + 30° (C=19.49 mg/2ml CHCl3).

The filtrate (from original filtration of Solid A above) is evaporated to dryness; this results in a pale tan solid B (5.77 g.). One-half gram of solid B is converted to the free base in 20% NaOH in water and extracted into chloroform. The organic (CHCl3) phase is dried over MgSO4 and evaporated to give 150 mg. of oil. This oil is converted to the hydrochloride salt in etheral HCl; crystallization in CH3OH/ether gives 100 mg. of trans-l-diamine (m.p. 240°–242° $[\alpha]_D^{22°}$ −28° (C=15.84 mg/2ml. chloroform).

EXAMPLE 34

Preparation of trans-d-2-(3,4-dichlorophenyl)-N-methyl-N-[2-(1-pyrrolidinyl)cyclohexyl]acetamide maleate.

Following the procedure of Example 14 but substituting the trans-1-2-(N-pyrrolidinyl)cyclohexyl-N-methylamine for the trans-diamine of Example 14 there is obtained a yellow oil, 50 mg. of which (0.14 millimole) is dissolved in ethyl ether; to this is added 15.7 mg. (0.14 millimole) of maleic acid dissolved in ethyl ether. The gummy oil which comes out is washed with distilled ether and crystallized in CH3OH to give 31 mg. of colorless well-defined rods (the titled product). Dried at 65° in vacuo for 3 hr. m.p. 199°–200° (dec.). $[\alpha]_D^{22°}$ +83° (C=18.65 mg/2ml. chloroform)

EXAMPLE 35

Preparation of trans-1-2-(3,4-dichlorophenyl)N-methyl-N-[2-1-pyrrolidinyl)-cyclohexyl]acetamide maleate Following the procedure of Example 14 but substituting the trans-d-2-(N-pyrrolidinyl)cyclohexyl-N-methylamine for the trans-diamine of Example 14 there is obtained a yellow oil which is further purified by high pressure liquid chromatography on a Merck micropacked silica gel column, eluting with 5% MeOH-CHCl3.v/v. The center fractions are collected, as they contain the desired product (TLC determination) and are evaporated to give a yellow oil, 50 mg. of which (0.14 millimole) is dissolved in ethyl ether. The maleate acid addition salt is prepared by addition of 15.7 mg (0.14 millimole) of maleic acid in ethyl ether. Crystallization from CH3OH gives the titled compound as a solid; this solid is dried in vacuo at 65° for 3 hrs. (38 mg; m.p. 199°–200°). $[\alpha]_D^{22°}$ −84° (C=15.46 mg/2 ml. CHCl3).

Resolution of the d- and l- isomers of the cis-diamine starting materials can be done similarly.

The following examples illustrate the preparation of pharmaceutical compositions containing the aminoamide compounds of this invention.

EXAMPLE 36

One thousand tablets for oral use, each containing 40 mg. of trans-N-methyl-[2-(3-hydroxypyrrolidinyl)-cyclohexyl]-2-(3,4-dichlorophenyl)acetamide hydrochloride as the essential active ingredient are prepared from the following ingredients:

Essential active ingredient — 40gm.

Dicalcium phosphate — 150gm.

Methylcellulose, U.S.P. (15 cps) — 6.5gm.

Talc — 20gm.

Calcium Stearate — 2.0gm.

The essential active ingredient and dicalcium phosphate are mixed well, granulated with 7.5% aqueous solution of methylcellulose, passed through a No. 8 screen and dried carefully. The dried granules are passed through No. 12 screen, mixed with the talc and stearate and compressed into tablets. These tablets are useful in the treatment of pain in adult humans at a dose of 1 tablet 1 to 4 times a day as needed.

EXAMPLE 37

One thousand two-piece hard gelatin capsules for oral use, each capsule containing 20 mg. of trans-N-methyl-N-[2-(N-pyrrolidinyl)cyclohexyl]-2-(3,4-dichlorophenyl)acetamide hydrochloride as the essential active ingredient are prepared from the following ingredients:

Essential active ingredient — 20 gm.

Lactose, U.S.P. — 100 gm.

Starch, U.S.P. — 10 gm.

Talc, U.S.P. — 5 gm.

Calcium stearate — 1 gm.

The finely powdered materials are mixed thoroughly, then filled into hard gelatin capsules of appropriate size.

One capsule 4 times a day is useful for the treatment of pain in adult humans.

EXAMPLE 38

One-piece soft elastic capsules for oral use, each containing 100 mg. of trans-N-methyl-N-[2-N-pyrrolidinyl)cyclohexyl]-2-(4-chlorophenyl)-propionamide as the essential active ingredient are prepared in the usual manner by first dispersing the powdered active material in sufficient corn oil to render the material capsulatable.

One capsule 2 times a day is useful in the treatment of pain in adult humans.

EXAMPLE 39

An aqueous oral preparation containing in each teaspoonful (5 ml.) 80 mg. of trans-N-methyl-N-[2-(3-acetoxy-1-pyrrolidinyl)cyclohexyl]-2-(3,4-dichlorophenyl)acetamide hydrochloride as the essential active ingredient is prepared from the following ingredients:

Essential active ingredient — 160 gm.

Methylparaben, U.S.P. — 7.5 gm.

Propylparaben, U.S.P. — 2.5 gm.

Saccharin Sodium — 12.5 gm.

Glycerin — 3,000 ml.

Tragacanth powder — 10 gm.

Orange oil flavor — 10 gm.

Orange II — 7.5 gm.

Deionized water, q.s. to — 10,000 ml.

The foregoing aqueous preparation is useful in the treatment of adult pain at a dose of 1 teaspoonful 4 times a day.

EXAMPLE 40

One thousand tablets for oral administration, each containing 10 mg. of trans-N-methyl-N-[2-(N-pyrrolidinyl)cyclohexyl]-2-(3,4-dichlorophenyl)acetamide hydrochloride as the essential active ingredient and 16.2 mg. of phenobarbital are prepared from the following ingredients:

Essential active ingredient, micronized — 10 gm.

Phenobarbital — 16.2 gm.

Lactose — 150 gm.

Starch — 15 gm.

Magnesium stearate — 1.5 gm.

The ingredients are thoroughly mixed and slugged. The slugs are broken down by forcing through a screen and the resulting granules are then compressed into tablets.

These tablets are useful in reducing post-surgical pain in dogs at a dose of 1 to 3 tablets depending on the weight of the animal and its condition.

EXAMPLE 41

A sterile aqueous suspension suitable for intramuscular injection and containing in each milliliter 50 mg. of the Example 36 essential active ingredient is prepared from the following ingredients:

Essential active ingredient — 5 gm.

Polyethylene glycol 4000, U.S.P. — 3 gm.

Sodium chloride — 0.9 gm.

Polysorbate 80, U.S.P. — 0.4gm.

Sodium metabisulfite — 0.1 gm.

Methylparaben, U.S.P. — 0.18 gm.

Propylparaben, U.S.P. — 0.02 gm.

Water for injection, q.s. to — 100 ml.

The preceding sterile injectable is useful in the treatment of pain at a dose of ½ to 2 ml.

EXAMPLE 42

One thousand suppositories, each weighing 2.5 gm. and containing 50 mg. of N-methyl-N-[2-(N,N-dimethylamino)cyclohexyl]-2-(4'-bromophenyl)acetamide as the essential active ingredient, are prepared from the following ingredients:

Essential active ingredient — 150 gm.

Propylene glycol — 165 gm.

Polyethylene glycol 4000 q.s. — 2,500 gm.

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of post-surgical pain at a dose of 1 suppository rectally twice a day.

The following examples illustrate pharmaceutical compositions containing the aminoamide compounds of this invention in combination with other drug compounds.

EXAMPLE 43

One thousand hard gelatin capsules for oral use, each containing 20 mg. of the Example 36 essential active ingredient and 40 mg. ketazolam are prepared from the following ingredients:

Essential active ingredient, micronized — 20 gm.

Ketazolam — 40 gm.

Starch — 125 gm.

Talc — 25 gm.

Magnesium stearate — 1.5 gm.

One capsule 4 times a day is useful in the relief of pain in adult humans.

EXAMPLE 44

Ten thousand scored tablets for oral use, each containing 80 mg. of N-methyl-N-[2-(N,N-dimethylamino)-cyclohexyl]-2-(3,4-dichlorophenyl)acetamide tosylate as the essential active ingredient and 32 mg. of caffeine are prepared from the following ingredients:

Essential active ingredient, micronized — 800 gm.

Caffeine — 320 gm.

Lactose — 1,500 gm.

Corn Starch — 500 gm.

Talc — 500 gm.

Calcium Stearate — 25 gm.

The ingredients are thoroughly mixed and slugged. The slugs are broken down by forcing through a number 16 screen. The resulting granules are then compressed into tablets each containing 80 mg. of the acetamide derivative essential active ingredient and 32 mg. of caffeine.

This combination of active materials is effective in reducing pain in adult humans. The dose is one-half of two tablets 3 times a day, depending on the severity of the condition.

EXAMPLE 45

Ten thousand tablets for oral use, each containing 60 mg. of trans-N-methyl-N-[2-(3-acetoxy-N-pyrrolidinyl)cyclohexyl]acetamide hydrochloride as the essential active ingredient and 0.5 mg. of methylprednisolone are prepared from the following ingredients using the procedure described in Example 40.

Essential active ingredient, micronized — 600 gm.

Methylprednisolone — 5 gm.

Lactose — 1,000 gm.

Corn Starch — 500 gm.

Talc — 500 gm.

Calcium Stearate — 25 gm.

These tablets are useful in treating adult humans suffering from arthritic pain by administering 1 tablet 3 times a day.

EXAMPLE 46

Ten thousand tablets for oral use, each containing 5 mg. of trans-N-methyl-N-[2-(N-pyrrolidinyl)cyclohexyl]-2-(3,4-dichlorophenyl)acetamide hydrochloride as the essential active ingredient and 320 mg. acetaminophen, are prepared from the following ingredients and using the procedure of Example 40.

Essential active ingredient, finely powdered — 50 gm.

Acetaminophen, finely powdered — 3,200 gm.

Corn Starch — 500 gm.

Talc — 500 gm.

Calcium stearate — 50 gm.

This tablet is useful in treating homotopic pain or headache in an adult patient by administering one or two tablets 3 times a day depending on the severity of the condition.

In similar formulations the acetaminophen can separately be replaced by aspirin (320 mg./tablet) or Phenacetin-Aspirin-Caffeine (P-A-C) compound (390 mg./tablet).

EXAMPLE 47

One thousand tablets for oral use, each containing 110 mg. of N-methyl-N-[2-(N',N'-dimethylamino)cyclohexyl]-2-(3,4-dichlorophenyl)acetamide maleate as an essential active ingredient and 400 mg. of chlorophenesin carbamate (Maolate) are prepared from the following ingredients:

Essential active ingredient, micronized (the maleate salt) — 110 gm.

Maolate — 400 gm.

Lactose — 50 gm.

Starch — 15 gm.

Magnesium stearate — 1.5 gm.

The ingredients are thoroughly mixed and slugged. The slugs are broken down by forcing through a screen and the resulting granules are then compressed into tablets.

These tablets are useful in reducing pain and muscle spasms at a dose of 1 tablet one to 3 times per day, depending upon the severity of the condition.

EXAMPLE 48

One thousand grams of ointment for topical use, each gram containing 20 mg. of N-methyl-N-[2-(N-pyrrolidinyl)cyclohexyl]-2-(3,4-dichlorophenyl)acetamide hydrochloride as the essential active ingredient is prepared from the following ingredients:

Essential active ingredient — 20 gm.

Spermaceti — 115 gm.

White wax — 110 gm.

Mineral oil — 560 gm.

Sodium borate — 5 gm.

Purified water q.s. to — 1,000 gm. (190 ml.)

Apply to site of pain 5 to 6 times daily.

EXAMPLES 49–66

Following the procedures of the preceding Examples 36 to 48, inclusive, similar dosage forms of other formula I compounds can be prepared by substituting an equivalent amount of the following compounds as the essential active ingredients; it is understood that these compounds can be the optically active or racemic cis or trans stereoisomers.

(49) N-methyl-N-[2-(N',N'-dimethylamino)cyclohexyl]-2-(4-bromophenyl)acetamide hydrochloride;

(50) N-methyl-N-[2-(N',N'-dimethylamino)cyclohexyl]-2-(4-trifluoromethylphenyl)acetamide hydrochloride;

(51) N-methyl-N-(2-(N'-methyl-N'-cyclopropylmethyl)cyclohexyl]-2-(4-bromophenyl)acetamide maleate;

(52) N-methyl-N-[2-(N',N'-dimethylamino)cyclohexyl]-2-(3-methoxyphenyl]acetamide;

(53) N-methyl-N-[2-(N',N'-dimethylamino)cyclohexyl]-2-(4-methylphenyl)acetamide hydrochloride;

(54) N-methyl-N-[2-(1-pyrrolidinyl)cyclohexyl]-2-(4-bromophenyl)acetamide hydrochloride;

(55) N-methyl-N-[2-(N',N'-dimethylamino)cyclohexyl]-2-(4-azidophenyl)acetamide;

(56) N-methyl-N-[2-(N',N'-dimethylamino)cyclohexyl]-2-(3,4-dichlorophenyl)acetamide tosylate;

(57) N-methyl-N-[2-(N',N'-dimethylamino)cyclohexyl]-2-(4-methoxyphenyl)acetamide hydrochloride;

(58) N-methyl-N-[2-[N'-(2-hydroxyethyl)-N'-methylamino]cyclohexyl]-2-(3,4-dichlorophenyl)acetamide hydrochloride;

(59) N-methyl-N-[2-(N'-butyl-N'-methylamino)cyclohexyl]-2-(3,4-dichlorophenyl)acetamide maleate;

(60) N-methyl-N-[2-(N',N'-diethylamino)cyclohexyl]-2-(3,4-dichlorophenyl)acetamide maleate;

(61) N-methyl-N-[2-(N',N'-dimethylamino)cyclohexyl]-2-(2,4,6-trimethylphenyl)acetamide hydrochloride;

(62) 1-(p-chlorophenyl)-N-[(2-dimethylamino)cyclohexyl]-N-methylcyclopropanecarboxamide;

(63) N-methyl-N-[2-(dimethylamino)cyclohexyl]-2-(2-naphthyl)acetamide hydrochloride;

(64) N-methyl-N-[2-(dimethylamino)cyclohexyl]-2-(1-naphthyl)acetamide hydrochloride;

(65) N-methyl-N-[2-(N',N'-dimethylamino)cycloheptyl]-2-(4-bromophenyl)acetamide maleate;

(66) N-methyl-N-[2-(N',N'-dimethylamino)cyclooctyl]-2-(4-bromophenyl)acetamide napsylate, or other equivalent pharmaceutically acceptable salts thereof.

Although not necessary in the embodiments of the inventive concept, additional active ingredients can be incorporated in the present pharmaceutical dosage unit forms as desired. For example, each pharmaceutical dosage unit form may contain therein an amount within the following non-toxic effective ranges: tranquilizers, anti-psychotic and anti-anxiety agents, such as chlorpromazine (5 to 50 mg.), thioridazine (5 to 200 mg.), haloperidol (0.5 to 5 mg.), meprobamate (100 to 400 mg.), chlordiazepoxide (5 to 50 mg.), diazepam (2 to 15 mg.), triazolam (0.25–1 mg.), ketazolam (5–300 mg.) and ectylurea (100 to 300 mg.); barbiturates, such as phenobarbital (8 to 60 mg.), butabarbital (8 to 60 mg.), and amobarbital (16 to 120 mg.); analgesics, anti-pyretics-anti-inflammatories, such as aspirin (150 to 600 mg.), flurbiprofen (20 to 200 mg.), ibuprofen (2 to 400 mg.), naproxen (20 to 200 mg.), indomethacin (20 to 200 mg.) and acetaminophen (150 to 600 mg.); and anti-depressants, such as amitriptyline hydrochloride (10 to 50 mg.), methylphenidate hydrochloride (5 to 20 mg.), d-amphetamine (5 to 20 mg.), d-amphetamine sulfate (2 to 15 mg.), methamphetamine hydrochloride (2 to 15 mg.), depending upon the condition being treated.

I claim:

1. A compound of the formula

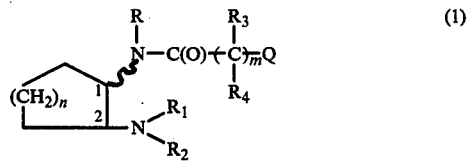

(1)

wherein the ∼ at the 1-position of the cycloaliphatic ring denotes trans-stereoconfiguration of the 1-position substituent with respect to the substituent in position 2 of the same cycloaliphatic ring;

R is $C_1$ to $C_3$-alkyl;

$R_1$ and $R_2$, taken separately, are $C_1$ to $C_3$-alkyl, or when $R_1$ is $C_1$ to $C_3$-alkyl, $R_2$ is $C_1$ to $C_6$-alkyl, $-CH_2CF_3$, $C_3$ to $C_6$-(allylic)alkenyl, $C_2$ to $C_5$-hydroxyalkyl, $C_3$ to $C_6$-cycloalkyl, $C_3$ to $C_4$-cycloalkylmethyl, phenyl-$C_1$ to $C_3$-alkyl, or $R_1$ and $R_2$ taken together with the nitrogen to which they are bonded complete a saturated, monocyclic, mononitrogen heterocyclic ring containing only carbon and nitrogen ring atoms and containing from 3 to 4 carbon atoms; said saturated monocyclic nitrogen heterocyclic rings having 3 to 4 ring carbon atoms permissively being substituted in the 3-position of the ring with hydroxy, $C_1$ to $C_3$-alkyloxy, or $C_1$ to $C_3$-alkanoyloxy; or N-piperazinyl ring, permissively substituted on the N'-nitrogen with a $C_1$ to $C_3$-alkyl;

$R_3$ is hydrogen or methyl;

$R_4$ is hydrogen or methyl, or $R_3$ and $R_4$ can be taken together with the carbon to which they are bonded to complete a cyclopropylene ring;

m is 1 to 4 and is 2 to 4 only when $R_3$ and $R_4$ are both hydrogen;

n is 2 to 4; and

Q is 1-naphthyl, 2-naphthyl or

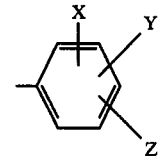

wherein each of X, Y and Z is hydrogen, a halogen having an atomic number of from 9 to 35, trifluoromethyl, $C_2$ to $C_3$-alkyl, $C_1$ to $C_3$-alkyloxy, azido or phenyl, and at least one of X, Y and Z is a substituent other than hydrogen, and when one of X, Y and Z is azido, phenyl, $C_1$ to $C_3$-alkyloxy or trifluoromethyl, the remaining X, Y and Z moieties are hydrogen, and the pharmaceutically acceptable salts thereof.

2. A compound according to claim 1 wherein R is $C_1$ to $C_3$-alkyl;
$R_1$ and $R_2$ are each $C_1$ to $C_3$-alkyl;
$R_3$ and $R_4$ are each hydrogen;
n is 2;
m is 1;
Q is

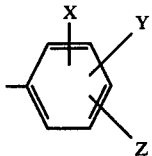

wherein at least one of X, Y and Z is a halogen having an atomic number of from 9 to 35, and pharmaceutically acceptable salts thereof.

3. A compound according to claim 2 in the trans-configuration wherein R is methyl;
$R_1$ and $R_2$ are each methyl;
$R_3$ and $R_4$ are each hydrogen;
n is 2;
m is 1;
Q is

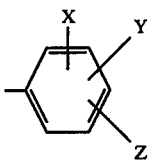

wherein X is bromo in the 4-position and Y and Z are hydrogen, and the pharmaceutically acceptable salts thereof.

4. A compound according to claim 2 in the trans-configuration wherein
R is methyl;
$R_1$ and $R_2$ are each methyl;
$R_3$ and $R_4$ are each hydrogen;
n is 2;
m is 1;
Q is

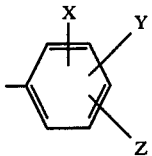

wherein X and Y are each chloro in the 3- and 4-positions and Z is hydrogen, and the pharmaceutically acceptable salts thereof.

5. A compound according to claim 1 wherein
R is $C_1$ to $C_3$-alkyl;
$R_1$ and $R_2$ are taken together with the nitrogen atom to which they are bonded to complete a saturated monocyclic mononitrogen heterocyclic ring containing from 3 to 4 ring carbon atoms;
$R_3$ and $R_4$ are each hydrogen;
n is 2;
m is 1, and
Q is

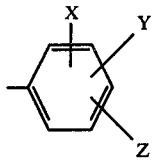

wherein at least one of X, Y and Z is a halogen having an atomic number of from 9 to 35, or azido, and pharmaceutically acceptable salts thereof.

6. A compound according to claim 5 in the trans-configuration wherein R is methyl;
$R_1$ and $R_2$ are taken together with the nitrogen to which they are bonded to complete a pyrrolidine ring;
$R_3$ and $R_4$ are each hydrogen;
n is 2;
m is 1; and
Q is

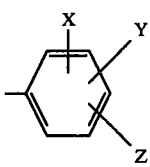

wherein X is bromo in the 4-position and Y and Z are hydrogen, and the pharmaceutically acceptable salts thereof.

7. A compound according to claim 5 in the trans-configuration wherein R is methyl; $R_1$ and $R_2$ are taken together with the nitrogen to which they are bonded to complete a pyrrolidine ring;
$R_3$ and $R_4$ are each hydrogen;
n is 2;
m is 1; and
Q is

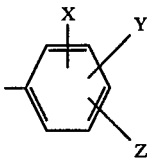

wherein X and Y are chloro in the 3 and 4-positions and Z is hydrogen and the pharmaceutically acceptable salts thereof.

8. A compound according to claim 7 which is trans-N-[2-(1-pyrrolidinyl)cyclohexyl]-N-methyl-2-(3,4-dichlorophenyl)acetamide hydrochloride.

9. A compound according to claim 1 wherein R is $C_1$ to $C_3$-alkyl;
$R_1$ and $R_2$ are taken together with the nitrogen to which they are bonded to complete a saturated monocyclic mononitrogen heterocyclic ring containing 3 to 4 carbon atoms;
$R_2$ is methyl and $R_4$ is hydrogen;
n is 2;
m is 1, and
Q is

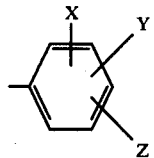

wherein at least one of X, Y and Z is a halogen having an atomic number of from 9 to 35 or azido, and if X is azido, Y and Z are hydrogen, and the pharmaceutically acceptable salts thereof.

10. A compound according to claim 9 in the trans-configuration wherein R is methyl;
$R_1$ and $R_2$ are taken together with the nitrogen atom to which they are bonded to complete a pyrrolidine ring,
R is methyl;
$R_3$ is methyl;
$R_4$ is hydrogen;
n is 2;
m is 1; and
Q is

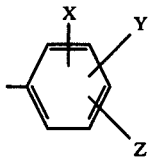

wherein X and Y are chloro in the 3- and 4-positions and Z is hydrogen, and the pharmaceutically acceptable salts thereof.

11. A compound according to claim 1 wherein R is $C_1$ to $C_3$-alkyl;
$R_1$ and $R_2$ are each $C_1$ to $C_3$-alkyl;
$R_3$ and $R_4$ are hydrogen;
n is 2;
m is 1;
Q is

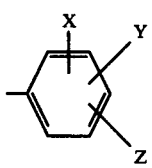

wherein at least one of X, Y and Z is $C_1$ to $C_3$-alkyl, and pharmaceutically acceptable salts thereof.

12. A compound according to claim 10 in the trans-configuration wherein R is methyl;
$R_1$ and $R_2$ are methyl;
$R_3$ and $R_4$ are hydrogen;
n is 2;
m is 1;
Q is

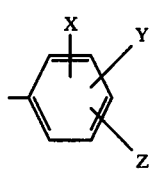

wherein X, Y and Z are each methyl, and the pharmaceutically acceptable salts thereof.

13. A compound according to claim 1 wherein R is $C_1$ to $C_3$-alkyl;
$R_1$ and $R_2$ are each $C_1$ to $C_3$-alkyl;
$R_3$ and $R_4$ are each hydrogen;
n is 3;
m is 1;
Q is

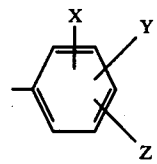

wherein at least one of X, Y and Z is a halogen having an atomic number of from 9 to 35, and pharmaceutically acceptable salts thereof.

14. A compound according to claim 13 in the trans-configuration wherein R is methyl;
$R_1$ and $R_2$ are methyl;
$R_3$ and $R_4$ are hydrogen;
n is 3;
m is 1;
Q is

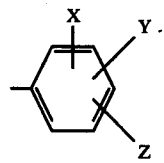

wherein X is bromo in the 4-position and Y and Z are each hydrogen, and the pharmaceutically acceptable salts thereof.

15. A compound according to claim 1 wherein R is $C_1$ to $C_3$-alkyl;
$R_1$ and $R_2$ are $C_1$ to $C_3$-alkyl;
$R_3$ and $R_4$ are each hydrogen;
n is 4;
m is 1; and
Q is

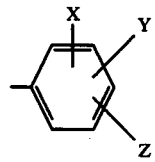

wherein at least one of X, Y and Z is a halogen having an atomic number of from 9 to 35, and pharmaceutically acceptable salts thereof.

16. A compound according to claim 15 in the trans-configuration wherein R is methyl;
$R_1$ and $R_2$ are each methyl;
$R_3$ and $R_4$ are each hydrogen;
n is 4;
m is 1; and
Q is

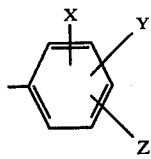

wherein X is bromo in the 4-position and Y and Z are hydrogen, and the pharmaceutically acceptable salts thereof.

17. A compound according to claim 1 wherein R is $C_1$ to $C_3$-alkyl;
 $R_1$ and $R_2$ are $C_1$ to $C_3$-alkyl;
 $R_3$ and $R_4$ are hydrogen;
 n is 2;
 m is 1; and
 Q is 2-naphthyl or 1-naphthyl, and the pharmaceutically acceptable salts thereof;

18. A compound according to claim 1 wherein the compound is trans-N-[2-(3-hydroxy-1-pyrrolidinyl)cyclohexyl]-N-methyl-2-(3,4-dichlorophenyl)acetamide, and the pharmaceutically acceptable salts thereof.

19. A compound according to claim 12 wherein the compound is trans-N-[2-(N,N-dimethylamino)cyclohexyl]-N-methyl-2-(2,4,6-trimethylphenyl)acetamide, and the pharmaceutically acceptable salts thereof.

20. A compound according to claim 17 wherein the compound is trans-N-[2-(N,N-dimethylamino)cyclohexyl]-N-methyl-2-(1-naphthyl)acetamide, and the pharmaceutically acceptable salts thereof.

21. A compound according to claim 1 wherein the compound is trans-N-[2-(3-acetoxy-1-pyrrolidinyl)cyclohexyl]-N-methyl-2-(3,4-dichlorophenyl)acetamide, and the pharmaceutically acceptable salts thereof.

22. A composition useful in pharmaceutically effective dosage unit form for alleviating pain in warm-blooded mammals which comprises a compound of formula I in claim 1 in combination with a pharmaceutically acceptable carrier.

23. A composition as defined in claim 22 wherein the compound of formula I therein is a compound of claim 5.

24. A composition as defined in claim 23 wherein the compound is trans-N-methyl-N-[2-(1-pyrrolidinyl)cyclohexyl]-2-(3,4-dichlorophenyl)acetamide, or a pharmaceutically acceptable salts thereof.

25. A method for alleviating pain which comprises administering to an animal suffering pain an effective amount of a compound of formula I in claim 1 in a pharmaceutical dosage unit form.

26. A method according to claim 25 wherein the effective amount of the compound of formula I in claim 1 ranges between about 0.5 and 350 mg of the compound per dose.

27. A method according to claim 26 wherein the active formula I compound is the compound of claim 7.

28. A compound according to claim 1 wherein the compound is trans-N-methyl-N-[2-(1-pyrrolidinyl)cycloheptyl]-2-(3,4-dichlorophenyl)acetamide, and its pharmacologically acceptable salts.

* * * * *